US012208178B2

(12) United States Patent
Segura et al.

(10) Patent No.: US 12,208,178 B2
(45) Date of Patent: Jan. 28, 2025

(54) MULTI-ARM BLOCK-COPOLYMERS FOR MULTIFUNCTIONAL SELF-ASSEMBLED SYSTEMS

(71) Applicant: THE REGENTS OF THE UNIVERSITY OF CALIFORNIA, Oakland, CA (US)

(72) Inventors: Tatiana Segura, Durham, NC (US); Nicolas Bernthal, Venice, CA (US); Weixian Xi, Pasadena, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1519 days.

(21) Appl. No.: 16/480,864

(22) PCT Filed: Jan. 30, 2018

(86) PCT No.: PCT/US2018/016016
§ 371 (c)(1),
(2) Date: Jul. 25, 2019

(87) PCT Pub. No.: WO2018/144481
PCT Pub. Date: Aug. 9, 2018

(65) Prior Publication Data
US 2019/0388583 A1 Dec. 26, 2019

Related U.S. Application Data

(60) Provisional application No. 62/452,914, filed on Jan. 31, 2017.

(51) Int. Cl.
*A61L 27/34* (2006.01)
*A61L 27/54* (2006.01)
*C08G 75/045* (2016.01)

(52) U.S. Cl.
CPC ............ *A61L 27/34* (2013.01); *A61L 27/54* (2013.01); *C08G 75/045* (2013.01); *A61L 2420/02* (2013.01); *A61L 2420/08* (2013.01)

(58) Field of Classification Search
CPC ...... A61L 27/34; A61L 27/54; A61L 2420/02; A61L 2420/08; C08G 75/045
See application file for complete search history.

(56) References Cited

U.S. PATENT DOCUMENTS

| | | | |
|---|---|---|---|
| 4,278,651 A * | 7/1981 | Hales | G01N 33/544 436/500 |
| 7,132,475 B2 | 11/2006 | Hubbell et al. | |
| 7,670,616 B2 | 3/2010 | Wu et al. | |
| 8,784,893 B2 | 7/2014 | Daniloff et al. | |
| 8,889,101 B2 | 11/2014 | Kannan et al. | |
| 9,700,492 B2 | 7/2017 | Bowman et al. | |
| 9,879,012 B2 | 1/2018 | Bowman et al. | |
| 10,017,510 B2 | 7/2018 | Bowman et al. | |
| 2005/0090008 A1 | 4/2005 | Segura et al. | |
| 2005/0147758 A1* | 7/2005 | Mao | G01N 33/5306 427/372.2 |
| 2009/0149941 A1 | 6/2009 | Hasson et al. | |
| 2010/0222407 A1 | 9/2010 | Segura et al. | |
| 2010/0260743 A1 | 10/2010 | Diwan et al. | |
| 2010/0266695 A1 | 10/2010 | Segura et al. | |
| 2012/0088862 A1 | 4/2012 | Abrami et al. | |
| 2014/0228453 A1* | 8/2014 | Bennett | A61P 1/00 514/772.6 |
| 2015/0104427 A1 | 4/2015 | Segura | |
| 2015/0202305 A1 | 7/2015 | Maynard et al. | |
| 2015/0359752 A1 | 12/2015 | Lu et al. | |
| 2016/0279283 A1 | 9/2016 | Griffin et al. | |
| 2017/0068018 A1* | 3/2017 | Qian | A61F 9/00781 |
| 2017/0368224 A1 | 12/2017 | Griffin et al. | |

(Continued)

FOREIGN PATENT DOCUMENTS

| | | |
|---|---|---|
| CN | 104628975 B | 3/2017 |
| EP | 3577179 B1 | 6/2024 |

(Continued)

OTHER PUBLICATIONS

Uygun et al. Influence of Type of Initiation on Thiol-Ene "Click" Chemistry, Macromol. Chem. Phys. 2010, 211, 103-110 (Year: 2010).*
Stavrakis et al. In Vivo Efficacy of a "Smart" Antimicrobial Implant Coating, J Bone Joint Surg Am. 2016;98:1183-9 (Year: 2016).*
First Communication pursuant to Article 94(3) EPC dated Nov. 3, 2022 for European Patent Appl. No. 18748384.7-1106, (4 pages).
The extended European search report dated Dec. 9, 2019 in European Patent Application No. 18748384.7, (7pages).
Communication pursuant to Rules 70(2) and 70a(2) EPC dated Oct. 4, 2019 in European Patent Application No. 17859271.3, (1 page).
Wang, Y. et al., A Novel Poly(amino amine)-Dendrimer-Based Hydrogel as a Mimic for the Extracellular Matrix, Adv. Mater. 2014, 26, 4163-4167.
Stavrakis, A. I. et al., In Vivo Efficacy of a "Smart" Antimicrobial Implant Coating, J Bone Joint Surg Am. 2016; 98:1183-9.

(Continued)

*Primary Examiner* — Robert A Wax
*Assistant Examiner* — John W Lippert, III
(74) *Attorney, Agent, or Firm* — VISTA IP LAW GROUP LLP

(57) ABSTRACT

A copolymer poly(ethylene glycol)-polyallyl mercaptan (PEG-PAM) material is used as a drug-containing coating for medical implants. In one embodiment, a mixture of multi-arm poly(ethylene glycol) (PEG), polyallyl mercaptan (PAM), a photoinitiator, organic solvent, and one or more drugs, medicaments, or pharmaceutical compounds is applied to a surface of the implant and is exposed to a polymerizing light source to form a PEG-PAM material coating that is formed in situ on the implant. The PEG-PAM coating may be used by surgeons to incorporate antibacterial drugs or the like into coatings that are applied in the operating room setting to medical devices such as orthopedic implants. The type of drug and dosing can be customized during the coating operation and tailored to the patient's needs. PEG-PAM may also be applied as a coating on or within tissue or an injectable gel.

9 Claims, 16 Drawing Sheets

(56) References Cited

U.S. PATENT DOCUMENTS

| | | | |
|---|---|---|---|
| 2017/0368237 A1* | 12/2017 | Leontein | .................. A61P 7/02 |
| 2018/0078671 A1 | 3/2018 | Griffin et al. | |
| 2018/0235898 A1 | 8/2018 | Lu et al. | |
| 2019/0142965 A1 | 5/2019 | Segura et al. | |
| 2019/0151497 A1 | 5/2019 | Griffin et al. | |

FOREIGN PATENT DOCUMENTS

| | | | |
|---|---|---|---|
| WO | WO-2006109014 A1 * | 10/2006 | ............... B05D 1/62 |
| WO | WO 2010/014799 | 2/2010 | |
| WO | WO 2014/098603 | 6/2014 | |
| WO | WO 2016/094533 | 6/2016 | |
| WO | WO-2016200337 A1 * | 12/2016 | ........... A61L 29/085 |
| WO | WO 2018/144481 | 8/2018 | |

OTHER PUBLICATIONS

PCT International Preliminary Report on Patentability (Chapter I of the Patent Cooperation Treaty) for PCT/US2018/016016, Applicant: The Regents of the University of California, Form PCT/IB/326 and 373, dated Aug. 15, 2019 (7 pages).

Reply to First Communication pursuant to Article 94(3) EPC dated Mar. 13, 2023 for European Patent Appl. No. 18748384.7-1106, (49 pages).

Response to the extended European search report (Rule 70a(2) EPC) dated Jul. 9, 2020, for European Patent Appl. No. 18748384.7-1106, (10 pages).

PCT International Search Report for PCT/US2018/016016, Applicant: The Regents of the University of California, Form PCT/ISA/210 and 220, dated Apr. 4, 2018 (3pages).

PCT Written Opinion of the International Search Authority for PCT/US2018/016016, Applicant: The Regents of the University of California, Form PCT/ISA/237, dated Apr. 4, 2018 (5pages).

Deubel, Frank et al., Polythioethers by Thiol-Ene Click Polyaddition of a,w-Alkylene Thiols, Micromol. Rapid Commun, 2013, 34, 1020-1025.

Kamaly, Nazila et al., Degradable Controlled-Release Polymers and Polymeric Nanoparticles: Mechanisms of Controlling Drug Release, Chem Rev. Feb. 24, 2016; 116(4):2602-2663. doi:10.1021/acs.chemrev.5b00346.

Liechty, William B., Polymers for Drug Delivery Systems, Annu Rev Chem Biomol Eng. 2010; 1:149-173. doi: 10.1146/annurev-chembioeng-073009-100847.

Stavrakis, Alexandra I. et al., In Vivo Efficacy of a "Smart" Antimicrobial Implant Coating, J Bone Joint Surg Am. 2016; 98:1183-9.

Deshmukh, M. et al., Abstract, Biodegradable poly(ethylene glycol) hydrogels based on a self-elimination degradation mechanism, Biomaterials. Sep. 2010; 31(26):6675-84. doi:10.1016/j.biomaterials.2010.05.21.

Hiemstra, Christine et al., Novel in Situ Forming, Degradable Dextran Hydrogels by Michael Addition Chemistry: Synthesis, Rheology, and Degradation, Macromolecules, 2007, 40(4), pp. 1165-1173.

The extended European search report dated Jun. 7, 2023 for European Patent Appl No. 21759925.7, Applicant: The Regents of University of California, (7 pages).

Communication pursuant to Rules 70(2) and 70a(2) EPC dated Jun. 27, 2024, Applicant: The Regents of University of California, (1 page).

Response to the extended European search report dated Jan. 8, 2024 for European Patent Appl No. 21759925.7, Applicant: The Regents of University of California, (29 pages).

Communication pursuant to Rules 70(2) and 70a(2) EPC dated Oct. 4, 2019 in European Patent Application No. 18748384.7, (1 page).

PCT International Preliminary Report on Patentability (Chapter I of the Patent Cooperation Treaty) for PCT/US2021/019485, Applicant: The Regents of the University of California, Form PCT/IB/326 and 373, dated Sep. 9, 2022 (6 pages).

Communication under Rule 71(3) EPC dated Jan. 10, 2024, for European Patent Application No. 18748384.7, (44 pages).

* cited by examiner ratio: stoichiometric ratio of allylsulfide and 1,3 propanedithiol

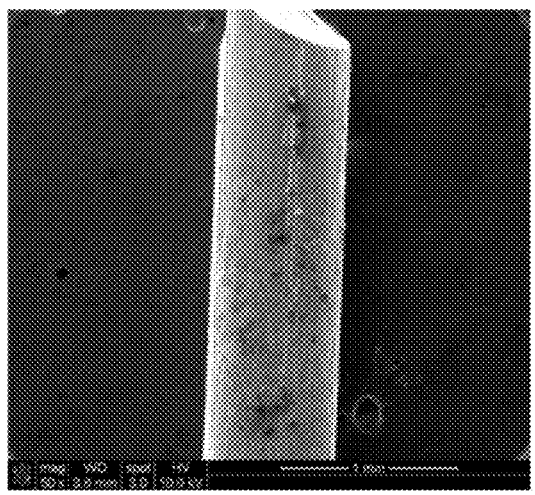
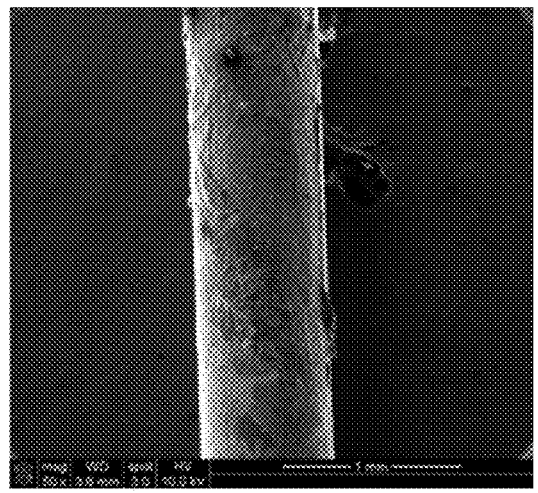
*FIG. 8A*  *FIG. 8B*
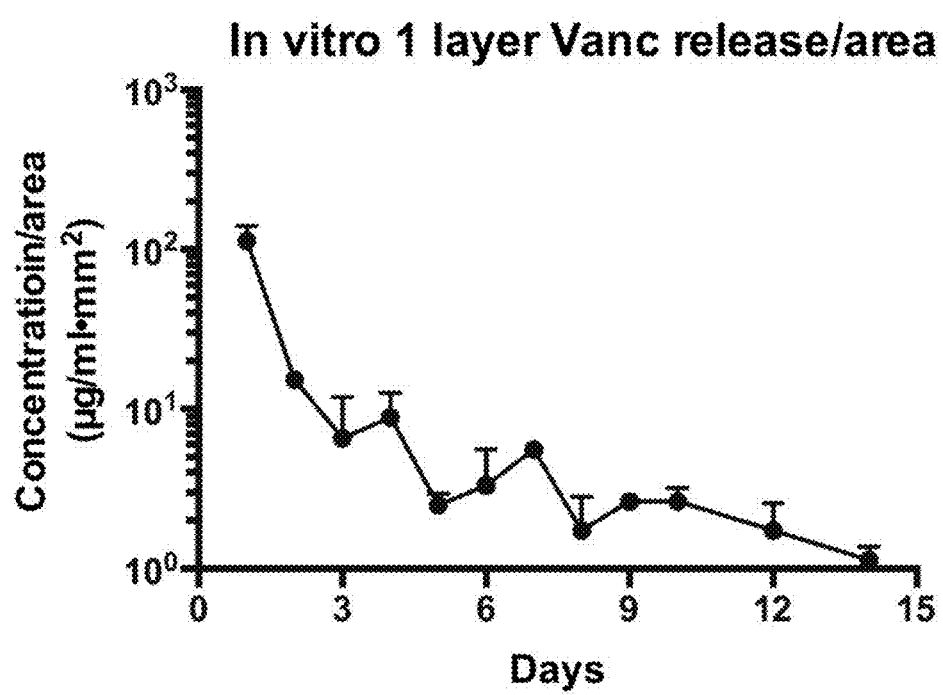
*FIG. 9*

MULTI-ARM BLOCK-COPOLYMERS FOR MULTIFUNCTIONAL SELF-ASSEMBLED SYSTEMS

RELATED APPLICATION

This Application is a U.S. National Stage filing under 35 U.S.C. § 371 of International Application No. PCT/US2018/016016, filed Jan. 30, 2018, which claims priority to U.S. Provisional Patent Application No. 62/452,914 filed on Jan. 31, 2017, which are hereby incorporated by reference. Priority is claimed pursuant to 35 U.S.C. §§ 119, 371 and any other applicable statute.

TECHNICAL FIELD

The technical field generally relates to the synthesis and use of multi-arm block-copolymers. In particular, the technical field relates to multi-arm block-copolymers that utilize polyallyl mercaptan (PAM). The use of PAM in conjunction with multi-arm poly(ethylene glycol) (PEG) has the ability to generate useful functional, biodegradable coatings that are useful for biomedical implants (e.g., orthopedic and other implants).

BACKGROUND

Orthopedic implant infections persist and cost the U.S. health system more than $8 billion per year in additional expenses, despite best efforts at host modification, environmental sterility, and systemic antibiotic therapy. Current standard of care for local antibiotic delivery is polymethylmethacralate (PMMA); a biologically inert delivery system with poor elution characteristics that is used for its mechanical properties, with local antibiotic delivery as a beneficial "secondary" function. As an alternative to PMMA, attempts have been made to engineer colloidal-based biodegradable systems with self-assembling block polymers as an alternative. For example, a "smart" implant coating using branched poly(ethylene glycol)-poly(propylene sulfide) (PEG-PPS) polymer has been designed to deliver antibiotics both passively and actively. See Stavrakis et al., In Vivo Efficacy of a "Smart" Antimicrobial Implant Coating, Journal of Bone and Joint Surgery, 98(14): 1183-89 (2016). However, these coatings have been labor-intensive to manufacture and thus required assembly prior to use in the operating room. This also has the unfortunate consequence of transforming conventional orthopedic implants into "drug delivery devices" that trigger additional burdensome regulatory approvals required by government agencies such as the Food and Drug Administration. For example, regulations on drug delivery devices have made factory-applied coatings impractical. Further, factory-coated implants increase the cost of all implants rather than allowing the surgeon to add a particular coating when the patient's risk-profile or other patient-specific circumstances warrant the coating's use. Factory-coated implants also suffer from the limitation that there is no versatility offered as each coating is loaded with the same antibiotic. This lack of personalization in the coating makeup is important because the physician may want to target a particular bacteria species that may be endemic to the geographical local area or local patient population. Factory-coated implants also may degrade over time limiting the overall shelf life of the implant device.

SUMMARY

In one embodiment, a polymeric delivery platform is disclosed for the delivery of medicinal or therapeutic compounds such as antibiotics that allows rapid assembly. In one embodiment, multi-arm poly(ethylene glycol) (PEG) is reacted with polyallyl mercaptan (PAM) in the presence of a photoinitiator and one or more drugs, medicaments, or pharmaceutical compounds and exposure to an appropriate light source (e.g., ultraviolet or UV light source) to form a PEG-PAM coating of material that may be formed in situ on, for example, one or more surfaces of a medical device.

The PEG-PAM coating permits medical devices such as orthopedic implants to remain sterile leaving industry or other storage warehouses and provides surgeons versatility to apply a drug-containing coating on a medical device or on or within the patient directly within the operating room. In some embodiments, the drug or medicament includes an antimicrobial agent or drug that can be applied directly to all or part of a medical device. The choice of antimicrobial agent used with the coating may be specifically tailored to the patient's needs.

A variety of modalities may be used to apply the drug-containing coating to the medical device surface or a tissue surface of the patient. For example, the coating may be applied as an aerosol such as a spray. The coating may also be applied as a paint using an applicator such as a brush or the like. The coating may also be applied to fill voids or spaces using an injection device such as a syringe. The applied coating is then, in one embodiment, subject to illumination from an appropriate wavelength-emitting light source (e.g., ultraviolet light source). The multi-arm block-copolymer based system described herein provides a cost-effective, practical alternative to PMMA that biodegrades, has consistent, tailorable release kinetics, and allows patient-specific tailoring of antibiotic loading. In other embodiments, the PEG-PAM material described herein may also be used as a coating on or within tissue or an injectable gel.

In another aspect of the invention, a method of manufacturing or synthesizing PAM is disclosed. The method includes forming PAM through radial polymerization of 1,3 propanedithiol and allylsulfide along with a photoinitiator such as 2,2-Dimethoxy-2-phenylacetophenone (DMPA). The mixture is then subject to polymerizing ultraviolet light for a period of time to synthesize PAM. Depending on the stoichiometric ratio mixture of 1,3 propanedithiol and allylsulfide that is used, the PAM may be thiol-terminated, allyl-terminated or both thiol-terminated and allyl-terminated. A 1:1 stoichiometric ratio mixture of 1,3 propanedithiol and allylsulfide generates PAM that is both thiol-terminated and allyl-terminated. A stoichiometric ratio mixture of 1,3 propanedithiol and allylsulfide with a ratio of 1,3 propanedithiol to allylsulfide that is greater than 1 produces PAM that is thiol-terminated. A stoichiometric ratio mixture of 1,3 propanedithiol and allylsulfide with a ratio of 1,3 propanedithiol to allylsulfide that is less than 1 produces PAM that is allyl-terminated. Notably, PAM is synthesized by radical polymerization as opposed to anionic polymerization as is the case with PPS.

In one embodiment, the thiol group of the PAM molecule can be used in various thiol-based click chemistries for polymer modification or functionalization. For example, PAM may be used in conjunction with Michael addition of multi-arm PEG-maleimide in the presence of triethylamine catalyst to synthesize multi-arm-PEG-PAM diblock polymers. In one embodiment, eight-arm PEG-maleimide was used to form the multi-arm-PEG-PAM diblock polymer. The molar ratio of PAM may be adjusted to alter the hydrophilicity/hydrophobicity of the synthesized polymer. For example, reducing the number of arms reacted with PAM to three (3) from eight (8) makes the block-copolymer water soluble.

In another embodiment, the allyl group of the PAM molecule can be used to synthesize a PEG-PAM copolymer coating using thiol contained PEG molecules using light activation. For example, multi-arm PEG-thiol molecules can be reacted with PAM in the presence of a photoinitiator and one or more drugs, medicaments, or pharmaceutical compounds under light illumination to form a coating or layer that is applied to one or more surfaces such as the surface of a medical device. In one particular embodiment, a mixture including PEG-thiol, PAM, a photoinitiator, and an antibiotic is applied to a surface of a medical device such as an orthopedic implant. The now-coated medical device is then subject to irradiation with polymerizing light (e.g., ultraviolet light).

In one embodiment, the process of coating one or more surfaces of a medical device and polymerizing the coating may be performed by the surgeon or physician inside a medical operating room. For example, a mixture or solution containing the PEG-thiol, PAM, and photoinitiator may be provided for use by the surgeon or physician. The surgeon or physician may add the desired drug(s), medicament(s), or pharmaceutical compound(s) to this mixture or solution prior to application. Alternatively, the PEG-thiol, PAM, and photoinitiator may already be pre-mixed with the drug(s), medicament(s), or pharmaceutical compound(s).

In another embodiment, a method of coating one or more surfaces of a medical device includes providing a mixture of polyallyl mercaptan (PAM), a multi-arm poly(ethylene glycol) (PEG), and a photoinitiator in an organic solvent containing one or more drugs, medicaments, or pharmaceutical compounds; applying the mixture to one or more surfaces of the medical device; and irradiating the mixture with polymerizing light to form a PEG-PAM coating on the one or more surfaces of the medical device containing the one or more drugs, medicaments, or pharmaceutical compounds.

In another embodiment, a coating material is formed from polymerized polyallyl mercaptan (PAM) and a multi-arm poly(ethylene glycol) (PEG), wherein the coating material contains one or more drugs, medicaments, or pharmaceutical compounds therein. The coating material, in one embodiment, is disposed on one or more surfaces of a medical device. In another embodiment, the one or more drugs, medicaments, or pharmaceutical compounds includes one or more antibiotics. The coating material may be applied in one or more layers.

In another embodiment, a method of making PEG-PAM copolymer containing a drug or pharmaceutical compound therein includes providing a mixture of polyallyl mercaptan (PAM), a multi-arm poly(ethylene glycol) (PEG), and a photoinitiator in an organic solvent containing one or more drugs, medicaments, or pharmaceutical compounds. The mixture is applied to the surface of a substrate such as a surface (or multiple surfaces) of a medical device or implant and the applied mixture is illuminated with polymerizing light.

In another embodiment, a method of making PEG-PAM copolymer includes providing a mixture of polyallyl mercaptan (PAM) and a multi-arm poly(ethylene glycol) (PEG) in an organic solvent and adding a catalytic amount of trimethylamine.

In another embodiment, a method of making polyallyl mercaptan (PAM) includes providing a mixture containing 1,3 propanedithiol and allylsulfide in the presence of a photoinitiator and illuminating the mixture with ultraviolet light.

BRIEF DESCRIPTION OF THE DRAWINGS

FIG. 8A illustrates scanning electron microscopic (SEM) images of the surfaces of a bare titanium pin (8-mm in diameter).

FIG. 8B illustrates a SEM image of a titanium pin coated with PEG-PAM containing vancomycin.

FIG. 9 illustrates a graph of the in vitro passive release (concentration/area) of a single layer of vancomycin containing PEG-PAM coated on the titanium pins. Quantified via UV-Vis, the daily release of vancomycin per pin over 14 days.

DETAILED DESCRIPTION OF THE ILLUSTRATED EMBODIMENTS

In one embodiment, a polymeric delivery platform is disclosed that is formed from a PEG-PAM copolymer of polyallyl mercaptan (PAM) and a multi-arm poly(ethylene glycol). The PEG-PAM copolymer system may be used for the delivery of medicinal or therapeutic compounds such as antibiotics to living tissue. The polymeric delivery platform, in one embodiment, is coated in situ on one or more surfaces of a medical device or implant that is to be used in a mammalian subject. In other embodiments, the polymeric delivery platform may be directly delivered to tissue or tissue regions of a mammalian subject. As explained herein, in one preferred embodiment, a multi-arm poly(ethylene glycol) (PEG) is reacted with polyallyl mercaptan (PAM) in the presence of an initiator compound (e.g., photoinitiator) and one or more drugs, medicaments, or pharmaceutical compounds. The mixture is exposed to an initiator source such as light, heat, or a redox initiator to polymerize the copolymer. In one embodiment, the initiator compound is a photoinitiator and the mixture is first applied to one or more surfaces of a medical device or implant and is then exposed to an appropriate polymerizing light source (e.g., ultraviolet light source or visible light source) to form a PEG-PAM copolymer coating or layer(s) that is formed in situ on the medical device or implant.

The PEG-PAM coating permits medical devices or implants to remain in a sterile state prior to use and provides surgeons the versatility to customize the drug, medicament, or pharmaceutical compound-containing coating on a medical device or implant (or applied on or within the patient directly within the operating room in other applications). In some embodiments, the drug, medicament, or pharmaceutical compound includes one or more antimicrobial agents or drugs that can be applied directly to all or part of a medical device or implant. The choice of antimicrobial agent used with the PEG-PAM coating may be specifically tailored to the patient's needs.

Figure 1:
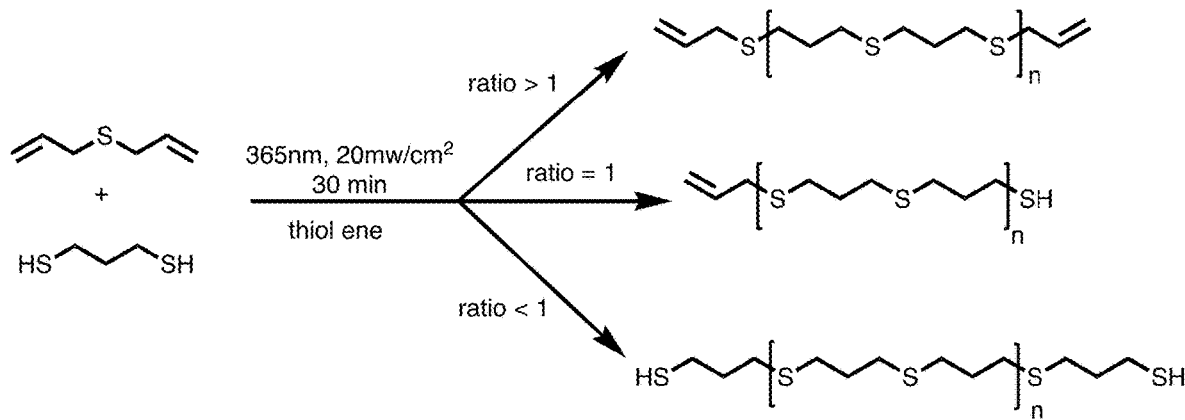
FIG. 1 illustrates the synthesis of PAM according to one embodiment from the radial polymerization of 1,3 propanedithiol and allylsulfide. The stoichiometric ratio of allylsulfide to 1,3 propanedithiol may be adjusted to control whether the terminal ends of the PAM are thiol groups, allyl groups, or both.

The PEG-PAM coating described herein uses PAM as one of the copolymer blocks. PAM was previously known to be created by thiol-ene click polyaddition of α,ω-alkylene thiols, for example, as described in Deubel et al., Polythioethers by Thiol-Ene Click Polyaddition of α,ω-Alkylene Thiols, Macromol. Rapid Commun., 34, 1020-1025 (2013). Unfortunately, this synthesis process is a multi-step process that takes a considerable amount of time. In one embodiment as explained herein, a new method of synthesizing PAM is disclosed. FIG. 1 illustrates this new method which involves the synthesis of PAM from radial polymerization of 1,3 propanedithiol and allylsulfide. The synthesis of PAM is based on the thiol-ene copolymerization between 1,3 propanedithiol and allyl sulfide which are both commercially available with high purity.

The polymerization may be performed under 365 nm UV light irradiation with the presence of a photoinitiator and, depending on the relative stoichiometric ratio of 1,3 propanedithiol and allylsulfide produces PAM that is either thiol terminated, allyl terminated, or thiol and allyl terminated. In particular, when the mixture of 1,3 propanedithiol and allylsulfide is in a 1:1 stoichiometric ratio PAM is formed that has ends that are both thiol and allyl terminated. When the mixture of 1,3 propanedithiol and allylsulfide has a stoichiometric ratio of allylsulfide to 1,3 propanedithiol that is greater than 1, the PEM ends are allyl terminated. Conversely, when the mixture of 1,3 propanedithiol and allylsulfide has a stoichiometric ratio of allylsulfide to 1,3 propanedithiol that is less than 1, the PEM ends are thiol terminated. The linear polymer that has thiol and/or allyl at the ends enables further functionalization from end groups. The degree of polymerization may vary from between 5-15 with the length controlled by monomer amount. It is important to note that the method of synthesis is completely different from that used for the synthesis of poly(propylene sulfide) (PPS). PAM is synthesized via radical polymerization while PPS is synthesized using anionic polymerization.

In one exemplary example of the synthesis of PAM, 1 mol % 2,2-Dimethoxy-2-phenylacetophenone (DMPA) photoinitiator was added to a 1:1 stoichiometric ratio mixture of 1,3 propanedithiol and allylsulfide and then the mixture was illuminated under 365 nm UV light (20 mw/cm$^2$) irradiation for 30 minutes. Next, the PAM product is precipitated in the presence of cooled methanol and dried as a white wax.

Figure 2:
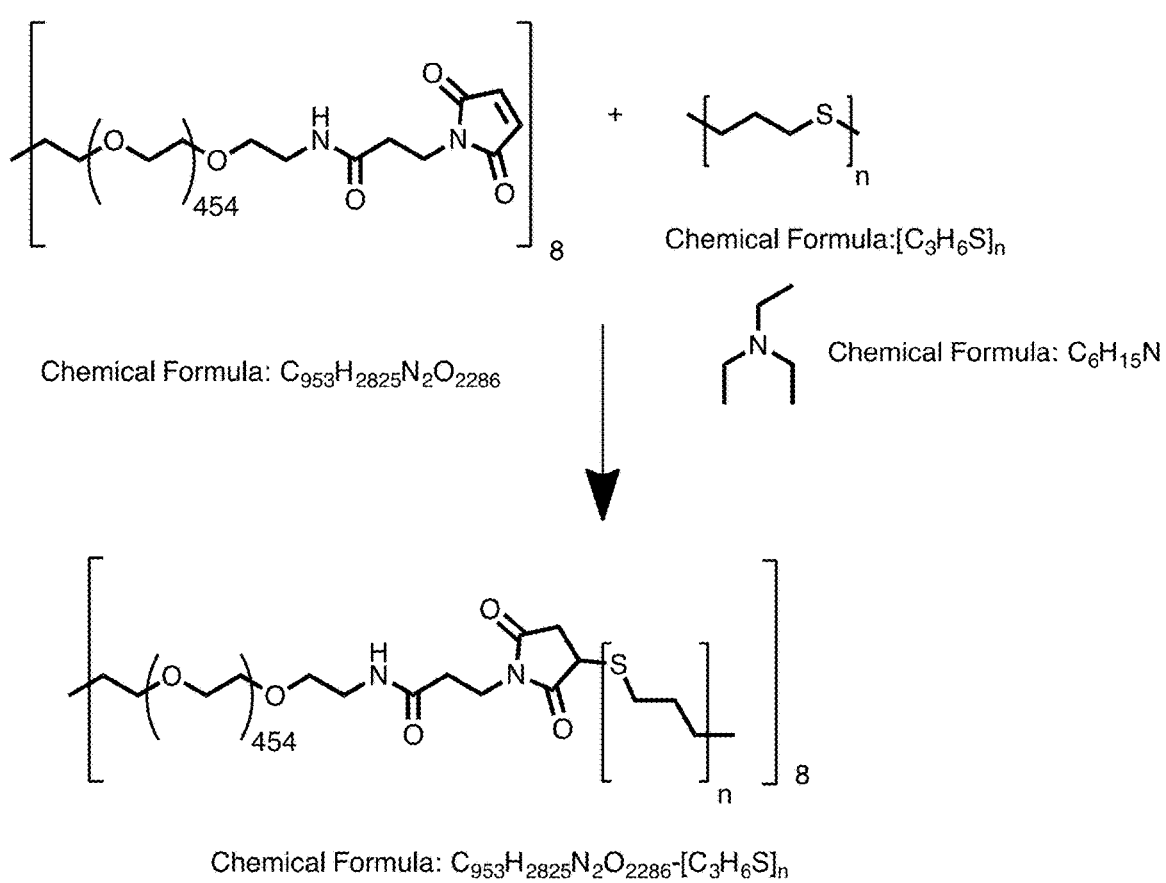
FIG. 2 illustrates the synthesis of PEG-PAM using a multi-arm PEG-maleimide and PAM in the presence of triethylamine (TEA) catalyst according to one embodiment.

PEG-PAM may be synthesized using the PAM described above in one of two synthesis methods. In a first synthesis method, PAM (n between 5 and 30) is conjugated with multi-arm PEG through any number of thiol reactive groups on the PEG molecule using a catalytic amount of base catalyst such as triethylamine (TEA). The reactive groups on PEG usable with this synthesis method include by way of example, PEG-acrylate, PEG-vinylsulfone, PEG-maleimide, PEG-acrylamide, PEG-isocyanate, PEG-bromide, and PEG-epoxide. FIG. 2 illustrates one example of the synthesis of PEG-PAM copolymer material using the multi-arm PEG-maleimide (e.g., eight arm) and PAM (n between 5 and 30) in the presence of triethylamine (TEA) catalyst. Any number of arms of for the multi-arm PEG may be used. Commercially available PEG with three (3), four (4), five (5), six (6), seven (7), eight (8) or more arms are available and usable with the synthesis method described herein. In this embodiment, PAM and the 8-Arm-PEG maleimide were dissolved in deuterated chloroform (CDCl$_3$) and a catalytic amount of triethylamine was added into the mixture and then stirred for 3 hours. The solvent was removed under vacuum and the crude product was precipitated in cold ether (4° C.).

Figure 3:
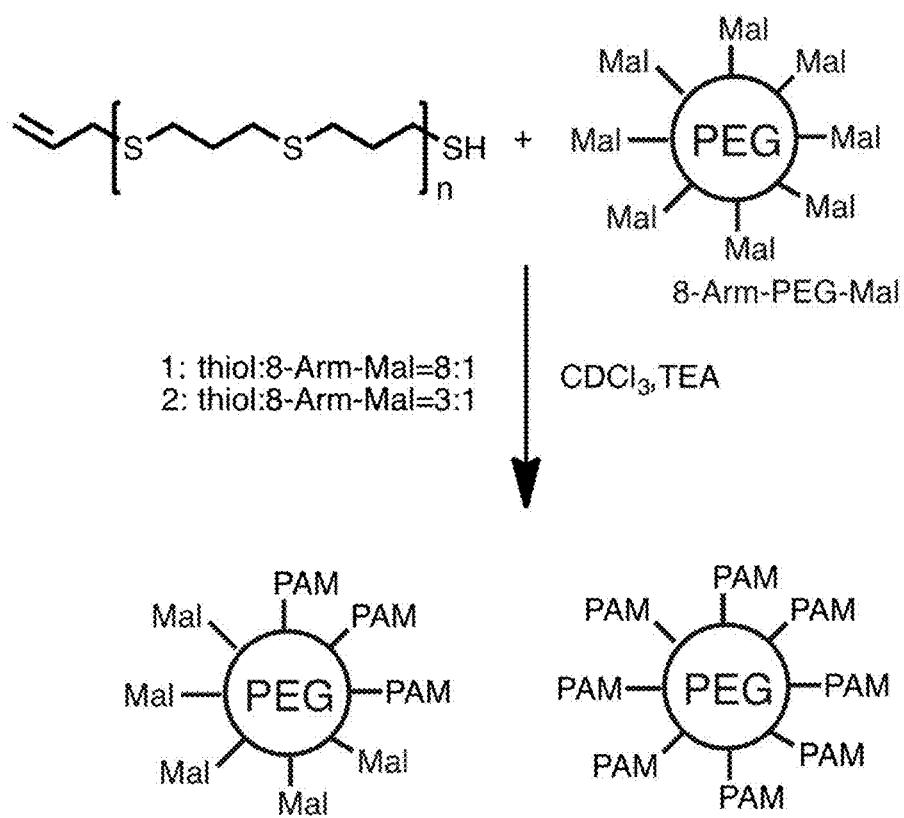
FIG. 3 illustrates a schematic representation of multi-arm PEG-PAM amphiphilic diblock polymer formed using different ratios of thiol to PEG-maleimide.

The thiol end group of PAM can be used in various thiol based click chemistries for polymer modification or functionalization. In this particular embodiment, thiol-maleimide was used for Michael addition to synthesize multi-Arm-PEG-PAM diblock polymers both starting from 8-Arm-PEG-maleimide (Mw: 40,000). The fully functionalized block polymer (8-Arm-PEG-PEG) was dissolved in the CDCl$_3$ (10 wt %) and instantly formed organogel, which is not soluble in water. If instead of reacting the eight (8) arms of the PEG with PAM, one only reacts three (3) arms, which would decrease the percentage of hydrophobic in the structure; the polymer is then water soluble. Generally, it is preferable to react the PAM with between three and five arms of the 8-Arm-PEG-maleimide as seen in FIG. 3. The degree to which PAM reacts with the arms of the PEG-maleimide structure may be controlled by the molar ratio of PAM to PEG-maleimide with a larger amount of PAM being used to react with a higher number of arms while a lower amount of PAM yields to fewer arms being occupied.

Figure 4:
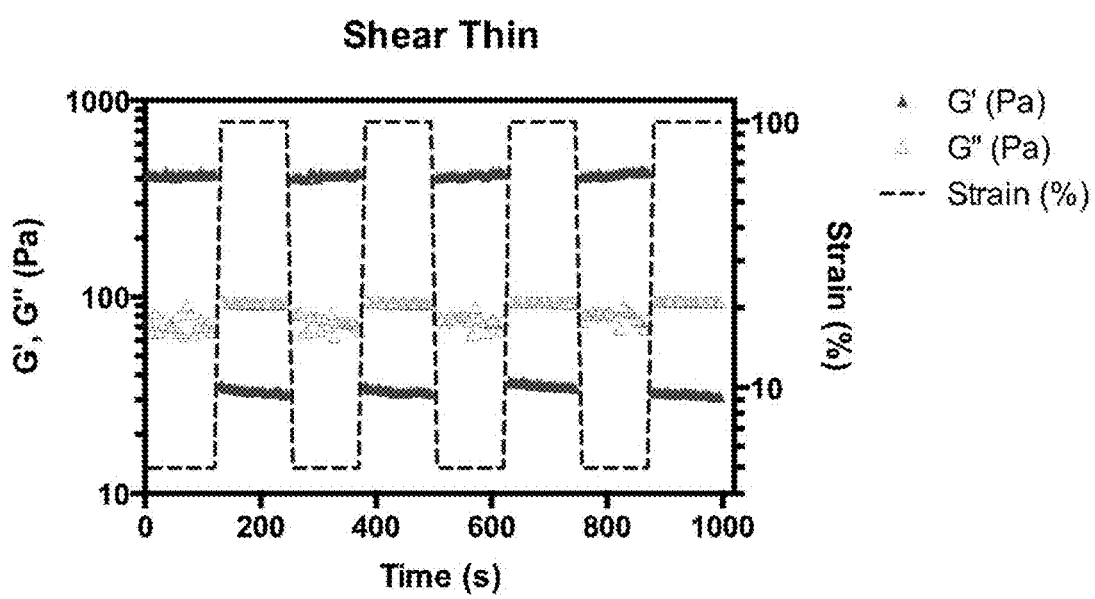
FIG. 4 illustrates dynamic strain amplitude cycles ($\gamma=5\%$ or 100%) of 5 wt % PEG-PAM hydrogel at a temperature of 25° C. The graph illustrates reversible shear-thinning behavior. Rheology measurement: PEG-PAM hydrogels were allowed to self-assemble for 30 min before transferred to an 8 mm plate-to-plate rheometer (Physica MCR 301, Anton Paar, Ashland, VA). An evaporation blocker system was used during measurements. For frequency sweep, the data were collected for the modulus with a frequency range of 0.1-100 rad/s under a 1% constrain at 37° C. For amplitude sweep, the data were collected for the modulus with a frequency of 10 rad/s under a constrain range of 0.1-100% at 37° C. A strain recovery experiment was performed with 4 cycles of strain steps of 1% and 50% strain, each at 6.5 rad/s.

The PEG-PAM copolymer is soluble in water at 5 wt % for stable hydrogel formation. Because the gelation mechanism is based on the hydrophobic interaction between PAM parts of the copolymer, it is expected to exhibit shear-thinning behavior like other supermolecular hydrogels such as PEG-PPS. Small amplitude oscillatory shear rheometry was performed to demonstrate the supermolecular interactions in PEG-PAM hydrogel. Strain sweeps at a constant oscillatory frequency of 6.5 rad/s at 25° C. revealed that the hydrogel could be disrupted under high strain condition. At higher applied strains ($\gamma$>10%) both G' (storage modulus) and G" (loss modulus) drop and G' decreases below G" at approximately $\gamma$=35% applied strain, indicative of a transition from gel-like to liquid-like state at high strain. The gel can rapidly recover its mechanical properties after high strain deformation, as evidenced by a dynamic step-strain test seen in FIG. 4. When a 5 wt % PEG-PAM hydrogel at 6.5% strain is subjected to an 100% step strain, G' drops substantially from G'=400 Pa to G'=30 Pa. Reversing the strain to 5% results in rapid recovery (<20 s) to be original modulus. This recovery process was performed several cycles, indicating very good self-healing property of the gels.

Figure 5A:
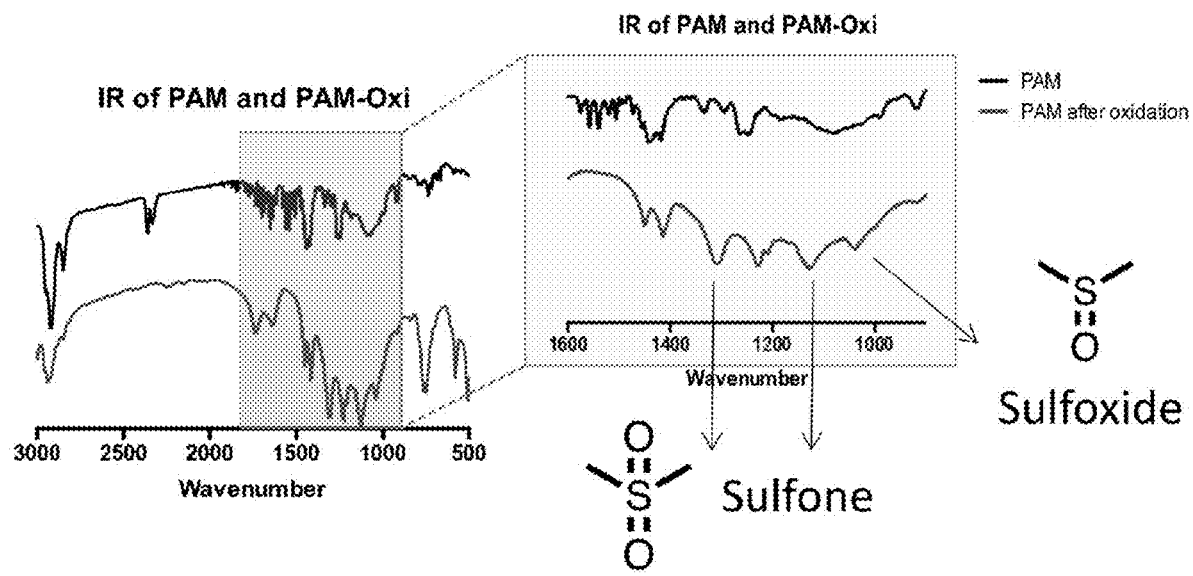
FIG. 5A illustrates FT-IR spectra of PAM and the oxidized forms. FT-IR Measurement: FT-IR spectra was collected by Jasco 420 FTIR Spectrophotometer. The sample pellet was prepared by mixing the 10 mg polymer and 500 mg KBr. GPC Measurement: Gel permeation chromatography/light scattering (GPC/LS) was performed on a SSI Accuflow Series III liquid chromatograph pump equipped with Wyatt DAWN EOS light scattering (LS) and Optilab rEX refractive index (RI) detectors. Separations were achieved using 105, 104, and 103 Å Phenomenex Phenogel 5 μm columns in chloroform. GPC/LS samples were prepared at concentrations of 5 mg/mL
Figure 5B:
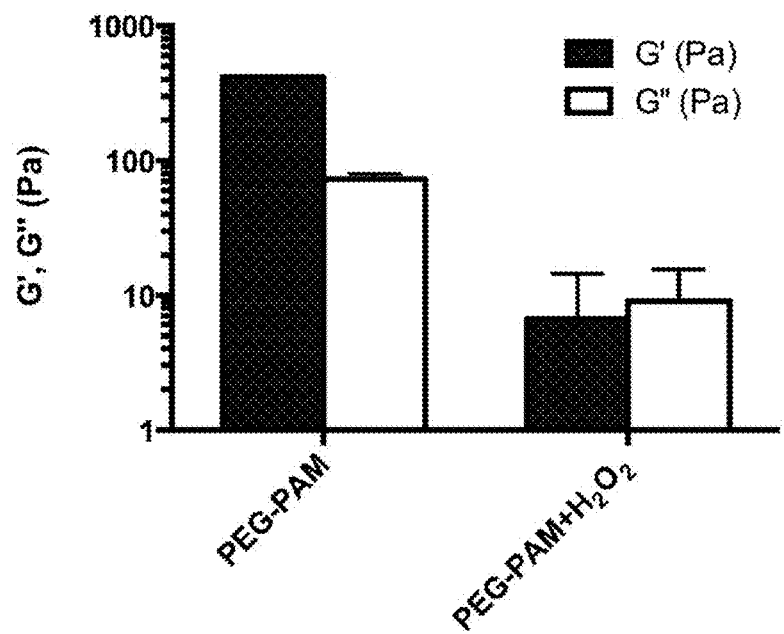
FIG. 5B illustrates the rheometry measurement of storage modulus and loss modulus of PEG-PAM before and after $H_2O_2$ treatment.

After the demonstration of physical cross-linked behavior of PEG-PAM hydrogel, another experiment was conducted to investigate the oxidation responsive behavior of this hydrogel because of the thio-ether backbone in the hydrophobic block. Thio-ether functional groups are very hydrophobic segments that enable the gelation of PEG-PAM, however, upon oxidation by peroxides or other reactive oxygen species, thio-ether backbones would be oxidized to sulfones or sulfoxides, which are so hydrophilic that cannot provide the physical interaction for gelation. According to this mechanism, thio-ether backbones have been widely employed in responsive materials for drug delivery. FT-IR was used to demonstrate the chemical transformation of thio-ether to sulfone/sulfoxide by monitoring the appearance of special peaks after $H_2O_2$ oxidation as seen in FIG. 5A. For oxidation studies, polythioether P2 (0.5 g) was dissolved in chloroform (50 mL) at 64° C. Subsequently 30% hydrogen peroxide solution (0.5 mL) was added to the reaction flask. After 2 h of reaction, the formed polymer was precipitated in a cold ether and dry in a vacuum oven at 50° C. The peak of 1100, 1300 cm$^{-1}$ and 1030 cm$^{-1}$ from FT-IR are assigned as the peaks of sulfone and sulfoxide respectively which provides direct proof of thio-ether oxidation. In addition, PEG-PAM gel can be also disrupted by treatment of $H_2O_2$ which induced dramatically decrease of modulus upon oxidation. FIG. 5B illustrates the rheometry measurement of storage modulus and loss modulus of PEG-PAM before and after $H_2O_2$ treatment.

Because the PEG-PAM copolymer could be disrupted by oxidative species, PEG-PAM polymer was further investigated as a coating material for use with medical devices and implants and in particular for orthopedic implants that would controllably release antibiotics or other drugs from the PEG-PAM polymer network. In this regard, another separate light polymerization-based synthesis method was investigated for the ability to polymerize PEG-PAM polymer directly on one or more surfaces of a medical device or implant. This second method of synthesizing PEG-PAM is used to form a coating on a substrate such as a medical device or implant (or even tissue). The coating is formed by polymerizing a mixture containing polyallyl mercaptan (PAM), a multi-arm poly(ethylene glycol) (PEG), an initiator, and one or more drugs, medicaments, or pharmaceutical compounds. Any number of arms of for the multi-arm PEG may be used. Commercially available PEG with three (3), four (4), five (5), six (6), seven (7), eight (8) or more arms are available and usable with the synthesis method described herein. In some embodiments, polymerization is initiated in response to applied stimulus that works in conjunction with the initiator. For example, the initiator may include a UV sensitive initiator such as DMPA and the mixture is polymerized by exposing the mixture to UV light. Likewise, the initiator may include a visible light sensitive initiator such as Irgacure 2959® (which can also be used for UV light). In yet another alternative, a thermal initiator may be used such as azobisisobutyronitrile (AIBN). In still another alternative, a redox initiator may be used such as ammonium persulfate (APS)/N,N,N,N-tetramethylethylenediamine (TMEDA). In one preferred embodiment that is used to coat substrates such as medical devices or implants, the initiator is a photoinitiator.

Figure 6A:
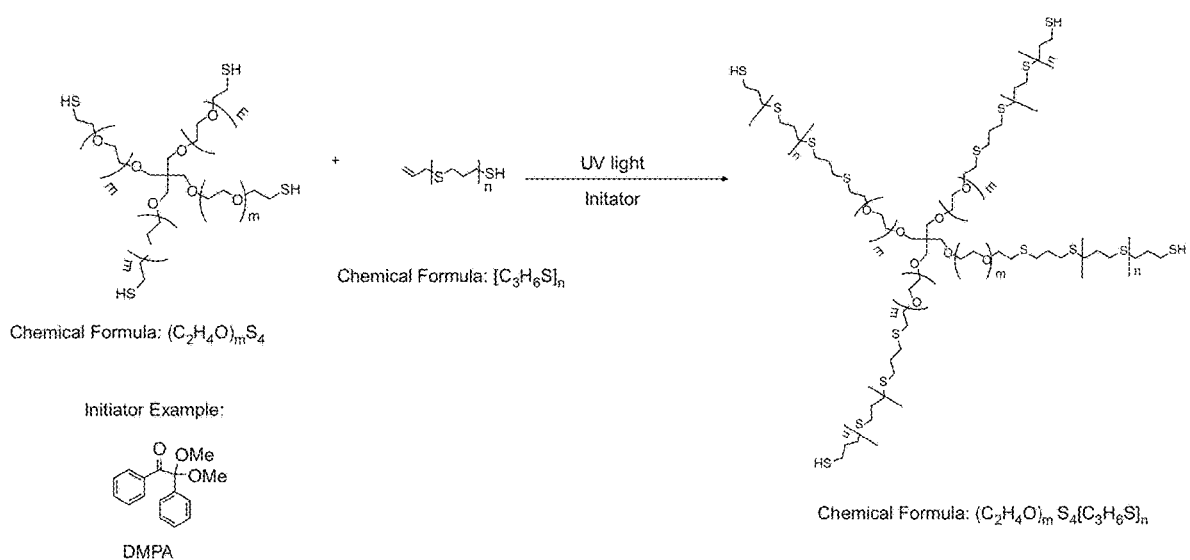
FIG. 6A illustrates the synthesis of PEG-PAM copolymer using an eight arm PEG-thiol, a photoinitiator (e.g., DMPA), and PAM. UV light is used to polymerize the mixture.

FIG. 6A illustrates one embodiment of the synthesis of PEG-PAM using a four-arm PEG. In this particular example, 4-arm PEG-thiol $(C_2H_4O)_mS_4$, wherein m is between 5 and 500, is mixed with PAM (in this example having allyl and thiol ends) having a chemical formula $[C_3H_6S]_n$, wherein n is between 5 and 30 in the presence of an initiator (e.g., DMPA) and a drug, medicament, or pharmaceutical compound contained in an organic solvent (not shown in FIG. 6A). The mixture is subject to UV light to form PEG-PAM having a chemical formula $(C_2H_4O)_mS_4[C_3H_6S]_n$.

Figure 6B:
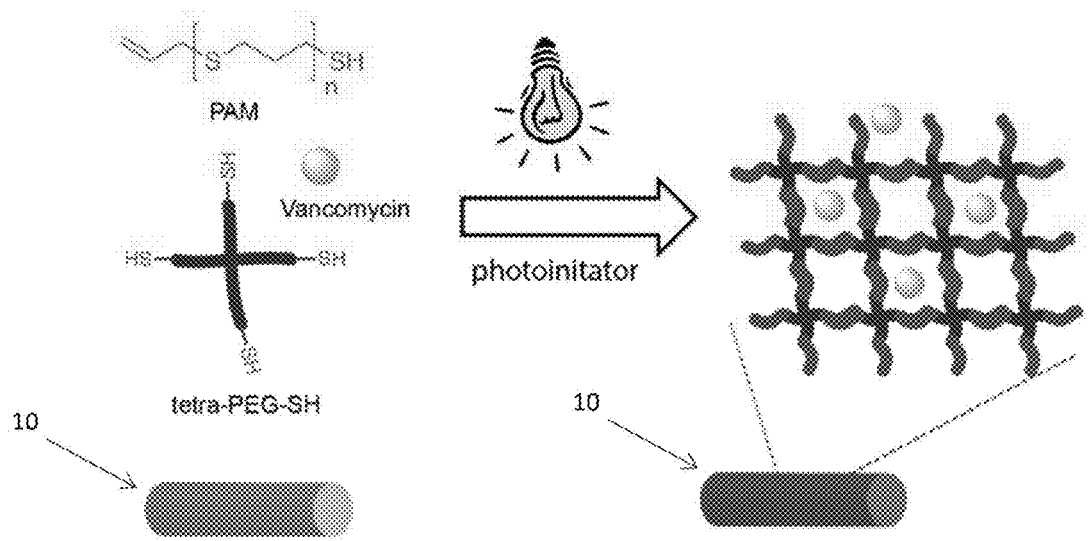
FIG. 6B schematically illustrates the formation of PEG-PAM copolymer on a medical device or implant containing a drug, medicament, or pharmaceutical compound therein using multi-arm PEG-thiol, a photoinitiator, and PAM. Ultraviolet light is used to polymerize the mixture.

The reactive groups on PEG usable with this synthesis method include by way of example, PEG-acrylate, PEG-vinylsulfone, PEG-maleimide, PEG-acrylamide, PEG-epoxide, PEG-thiol, PEG-norborene, PEG-vinyl, PEG-allyl, and PEG-alkyne. In this synthesis method, an initiator such as DMPA is used along with UV light to form the PEG-PAM copolymer from PEG and PAM as well as the drug, medicament, or pharmaceutical compound (which is omitted from FIG. 6A) and an organic solvent. FIG. 6B schematically illustrates one embodiment of a method of coating one or more surfaces of a medical device or implant 10. The medical device or implant 10 may include, by way of illustration and not limitation, an orthopedic implant, a spinal implant, a joint replacement device, pacemakers, insulin pumps, surgical pins, screws, or other surgical hardware. Typically, the coating is applied to a metallic surface of the medical device or implant 10 such as titanium or stainless steel but it should be appreciated that the coating and method of use is not limited to the particular composition of the substrate on which the coating resides. For example, it may also be applied to polymer or ceramic surfaces. In the particular example of FIG. 6B, PAM and a four-arm PEG-SH are mixed with a drug, medicament, or pharmaceutical component along with a small amount of organic solvent such as chloroform. Other organic solvents that may be used include dichloromethane (DCM), chloroform, and dimethyl sulfide (DMS). The amount of organic solvent may vary but is typically under 10% weight basis (e.g., 6% by weight). In the example of FIG. 6B, the drug that is incorporated into the PEG-PAM coating is the antibiotic vancomycin. It should be appreciated that other drugs, medicaments, and pharmaceutical compounds may be loaded within the PEG-PAM coating. Because of the use of the organic solvent, the drugs, medicaments, or pharmaceutical compounds should generally be dissolvable or soluble is organic solvents. It should also be appreciated that more than one type of drug, medicament, or pharmaceutical compounds may be carried by the coating or gel formed by the methods described herein.

Figure 7:
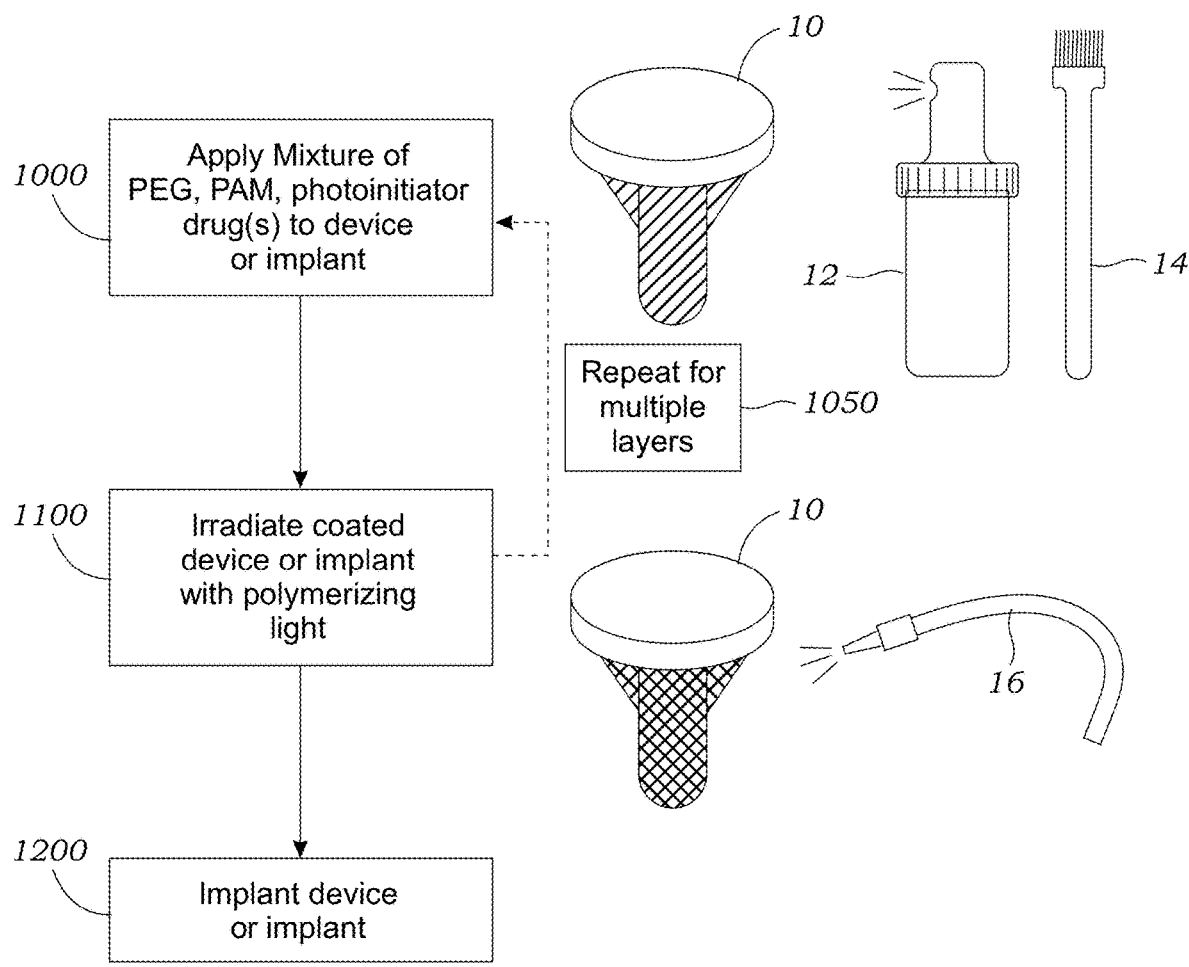
FIG. 7 illustrates a process for applying or forming a PEG-PAM coating on medical device or implant according to one embodiment.

In the operating room or other surgical setting, as best seen in FIG. 7, the surgeon or physician is provided with or assembles the mixture of PEG, PAM, initiator, organic solvent, and the drug, medicament, or pharmaceutical compound. The relative amounts of PEG and PAM in the mixture depends on the type of PEG used and the number of arms that are intended to be occupied. For example, for a four-arm PEG molecule, there typically would be PAM in a 4× (molar basis) so that all the PEG arms are bound to PAM. The amount of drug, medicament, or pharmaceutical compound that is added may vary. A typical concentration of the drug, medicament, or pharmaceutical compound is generally within or below about 10-20 mg/mL of mixture of PEG and PAM.

This mixture may be added to a delivery device such as spray bottle 12 or the like that can be used to spray a coating onto the medical device or implant 10 (other applicators such as an air-brush type applicator may also be used). The spray bottle 12 may actuated to apply a generally uniform coating of the mixture onto one or more surfaces of the medical device or implant 10 as seen in operation 1000 of FIG. 7. Alternatively, medical device or implant 10 may be coated with the mixture including PEG, PAM, initiator, and drug with an applicator 14 such as a brush. As yet another alternative, the medical device or implant 10 may be dipped into the mixture and removed. Next, as seen in operation 1100, the medical device or implant 10 is irradiated with light from a light source 16 (e.g., visible or UV light depending on the initiator) to polymerize the PEG-PAM polymer directly on one or more surfaces of the medical device or implant 10. The light source 16 may include a light, gun, wand, or other device that is typically found in hospitals and other medical settings and is used to illuminate a surface with light. The coating is illuminated for a short period of time (e.g., less than 5 minutes) to properly form the PEG-PAM copolymer. After applying the coating to the medical device or implant 10 some amount of time may elapse to enable the solvent to evaporate prior to illumination. This optional waiting period may last a few minutes. Thus, polymerization takes place in situ on the surface of the medical device or implant 10.

As seen in FIG. 7, multiple layers may optionally be coated on the surface of the medical device or implant 10 as seen by operation 1050. For multiple layers, the mixture is applied and then subject to irradiation followed by application of another layer of the mixture followed by irradiation. This can proceed for a number of cycles to create the desired thickness or number of layers on the medical device or implant 10.

In some embodiments, only a portion of the surface of the medical device or implant 10 is coated. For example, it may be preferred that only those surfaces that are in contact with bone or bodily tissue are to be coated. Those surfaces that serve as contact or articulating surfaces for other components may not be coated. The coating system described herein may be used with any number of medical devices or implants 10 but has particular suitability to joint replacement devices. The coating system may be used also with orthopedic trauma implants or spinal implants. Other implantable medical devices may also be coated such as pacemakers, insulin pumps, and the like. The surfaces that are coated are typically metal such as titanium, stainless steel, cobalt-chrome although other materials may also be coated. These include plastics, ceramics, as well as allograft cadaver bone.

In the above embodiment, the initiator is a photoinitiator which requires activation by light. It should be understood that in other embodiments, a heat applicator may be used to apply heat when the initiator is a thermal initiator. In other embodiments, for example, where the initiator is a redox initiator, there may be no need for a separate stimulation device. The process from start to finish is may be accomplished relatively quickly, for example, under 10 minutes (e.g., around 5 minutes) depending on the number and size of surfaces to be coated. Finally, as seen in operation 1200, the medical device or implant 10 is implanted in the subject.

PEG-PAM polymers loaded with antibiotic (vancomycin) were coated on the surface of titanium pins (i.e., K-wires) through in situ UV coating as described above which greatly reduced the amount to time compared with traditional methods. For the in situ UV-coating of PEG-PAM on titanium pins, 4-arm PEG-thiol and PAM polymers were dissolved in dichloromethane (DCM) to make 6% (w/v) solution, which was used to dissolve vancomycin at concentration of 20 mg/ml. The K-wires were submerged in the antibiotic-encapsulated polymer solution 1 min and later taken out allowing evaporation of DCM. Then the wires were irradiated with 365 nm UV light (20 mw/cm$^2$) for 1 min. The surface features of the polymer coatings was confirmed by SEM and more detailed elemental analysis also provided the proof about chemical elements derived from PEG-PAM. FIG. 8A illustrates scanning electron microscopic (SEM) images of the surfaces of a bare titanium pin (8-mm in diameter) and FIG. 8B illustrates a SEM image of a titanium pin coated with PEG-PAM containing vancomycin. The coating thickness is ~2 µm which is an inconsequential amount for press fit implants.

Figure 10:
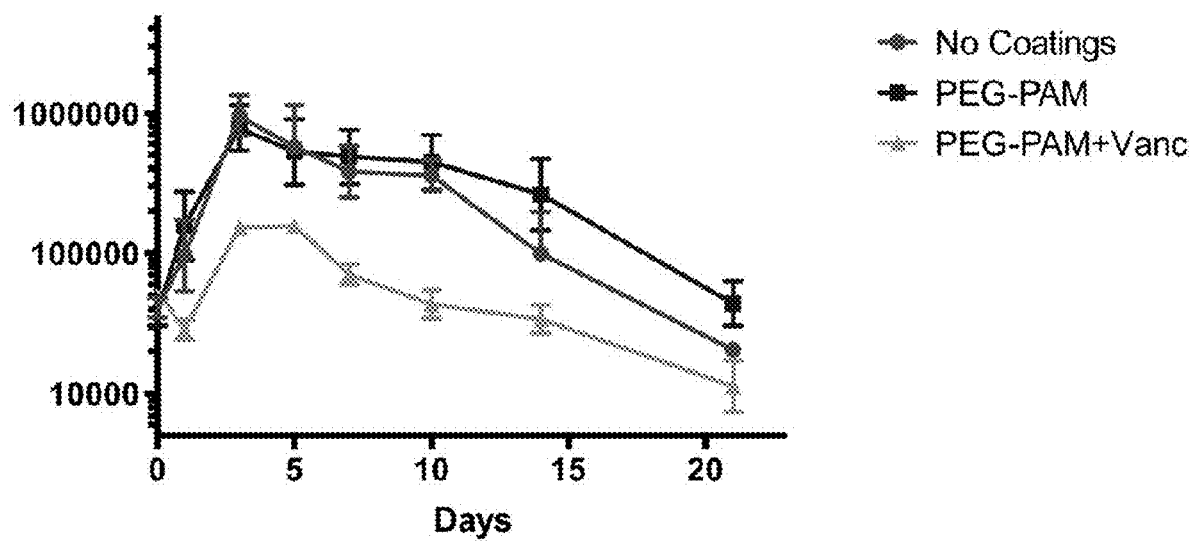
FIG. 10 illustrates postoperative in vivo S. aureus bioluminescence signals (logarithmic scale). Bioluminescence was measured using an IVIS® Spectrum (PerkinElmer).

The in vitro elution of vancomycin from the PEG-PAM coating on the pins was also evaluated. FIG. 9 illustrates a graph of the in vitro passive release of a single layer of vancomycin containing PEG-PAM coated on the titanium pins. The daily release results indicated the concentration of vancomycin maintained above the minimum inhibition concentration (MIC) for 14 days. The PEG-PAM coated pins were subject to an in vivo assay to measure their antibacterial efficacy. The in vivo assay employed bioluminescent *Staphylococcus aureus* Xen36 strain that naturally produces a blue-green light emitted only by metabolically active bacteria as an "indicator" that reflects bacterial infections. Uncoated pins, coated pins with PEG-PAM and coated pins with PEG-PAM containing vancomycin were implanted into the femoral intramedullary canal of a mouse in a retrograde fashion and inoculated with the *S. aureus*. The results from monitoring the bioluminescent signal indicated the vancomycin containing PEG-PAM pins has significantly lower signal comparing with other two groups within 21 days after implantation as seen in FIG. 10.

Figure 11:
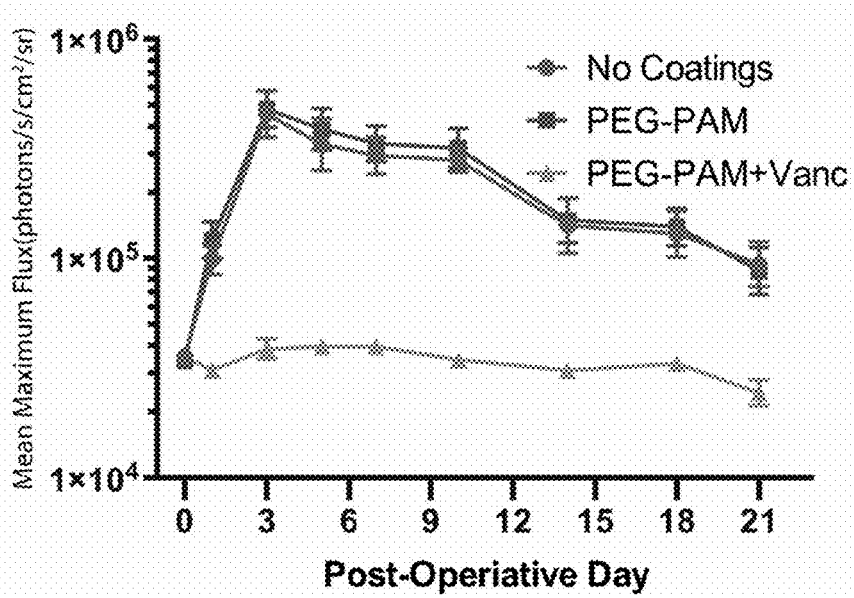
FIG. 11 illustrates a graph of bioluminescence as a function of time for the pin with no coating, pin with PEG-PAM, and pin with PEG-PAM loaded with vancomycin.
Figure 12:
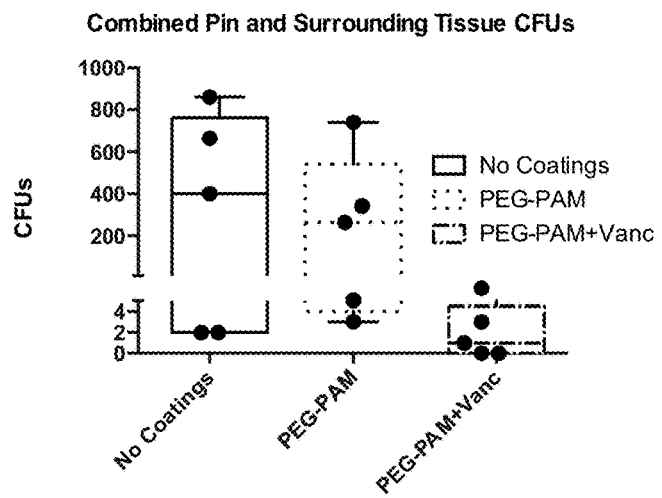
FIG. 12 illustrates a graph of colony-forming unit (CFU) enumeration from implants and peri-implant tissue for implants with no coatings PEG-PAM coating (no drug), and PG-PAM (with vancomycin).

In addition, in vivo data showed that four-arm PEG-PAM loaded titanium implants with vancomycin completely eradicated the infection after bacterial challenge. In this experiment, titanium pins as described herein (e.g., made with 4-arm PEG like FIG. 6A) were coated and implanted as described above. The pins were loaded with PEG-PAM/vancomycin. Impressively, as seen in FIG. 11, PEG-PAM loaded with vancomycin completely eradicated the infection, with no bacteria seen throughout the experiment. In contrast, the control PEG-PAM only or implant only controls retained high levels of bacteria throughout the study. Colony-forming unit (CFU) enumeration, as seen in FIG. 12, from implants and peri-implant tissue demonstrated a complete absence of bacteria in the polymer-vancomycin group, compared to more than 500 CFUs in both control groups.

Figure 13:
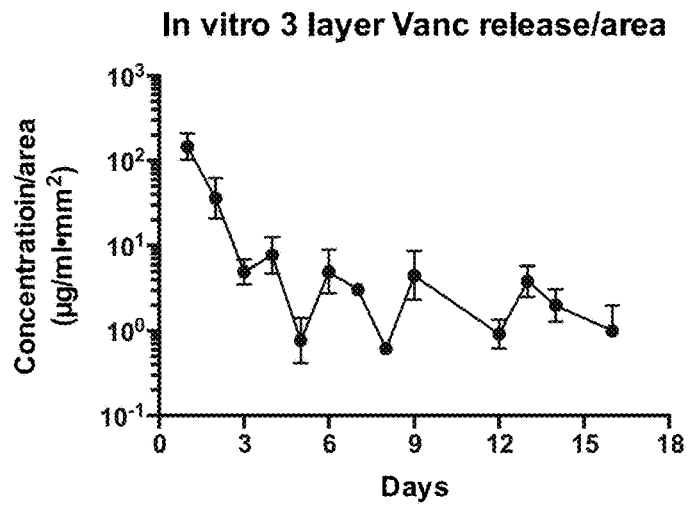
FIG. 13 illustrates a graph showing the release profile (release/area) from three (3) layers of PEG-PAM coating on a titanium K-wire implant.
Figure 14:
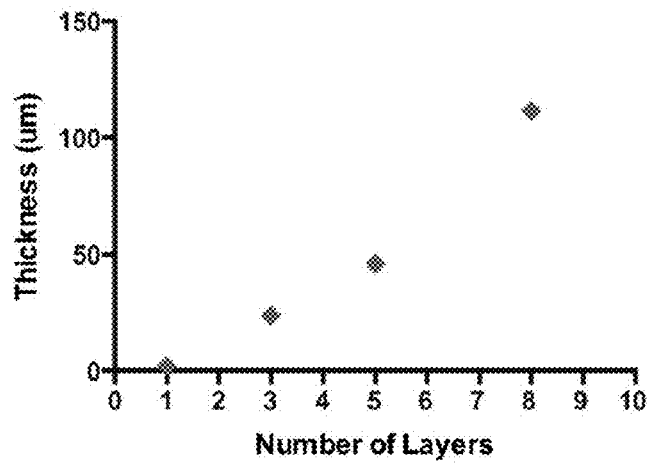
FIG. 14 illustrates a graph of the thickness of a single layer and multiple layers deposited on a K-wire implant. Data is shown for a single layer, three layers, five layers, and eight layers.
Figure 15:
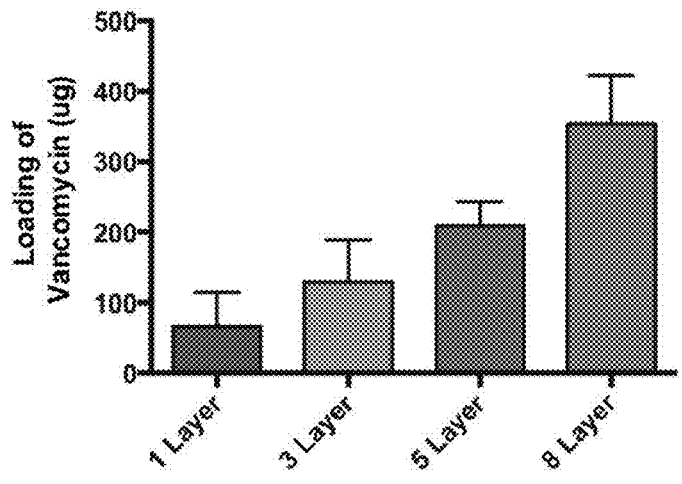
FIG. 15 is a graph showing the loading of vancomycin for coatings having a single layer, three layers, five layers, and eight layers.
Figure 16:
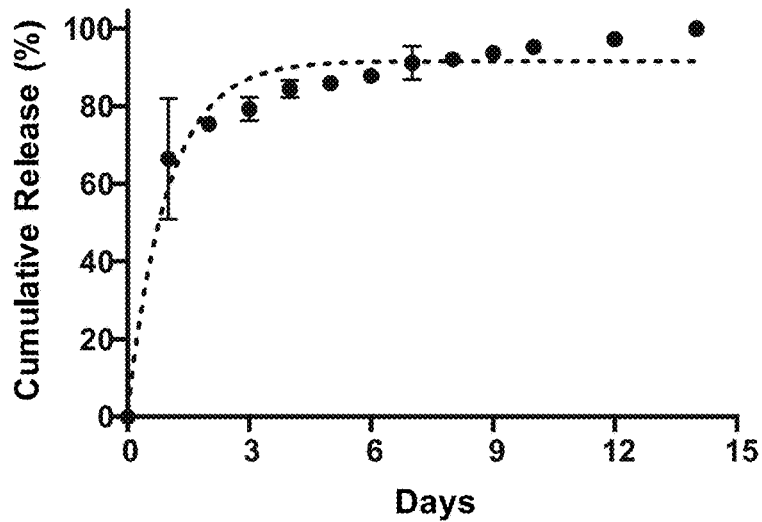
FIG. 16 is a graph showing the cumulative release percentage of vancomycin from a single layer of vancomycin-containing PEG-PAM coated on a titanium pin.

It should be understood that multiple separate layers of PEG-PAM containing the drug, medicament, or pharmaceutical composition may be applied to a medical device or implant 10. FIG. 13 illustrates the release profile from three (3) layers of PEG-PAM coating on a titanium K-wire implant. Thus, one can tailor the release profile by using fewer or more layers of coating. A larger total release of a drug, medicament, or pharmaceutical compound can be accomplished using multiple layers. The thickness of the PEG-PAM coatings increases with the number of coating layers that are applied to the medical device or implant 10. FIG. 14 illustrates the thickness of the resultant layer(s) on a K-wire implant for a single layer, three layers, five layers, and eight layers. A general linear relationship exists between the number of layers and the total thickness of the applied coating. FIG. 15 illustrates that by increasing the number of layers of PEG-PAM coating, the loading of a drug, medicament, or pharmaceutical compound (in this example vancomycin) is increased. FIG. 16 illustrates a graph showing the cumulative release of vancomycin from a single layer of vancomycin-containing PEG-PAM coated on a titanium pin. As seen in FIG. 16 after about 3 days most of the vancomycin was released. In this experiment, the vancomycin was released relatively quickly.

Figure 17:
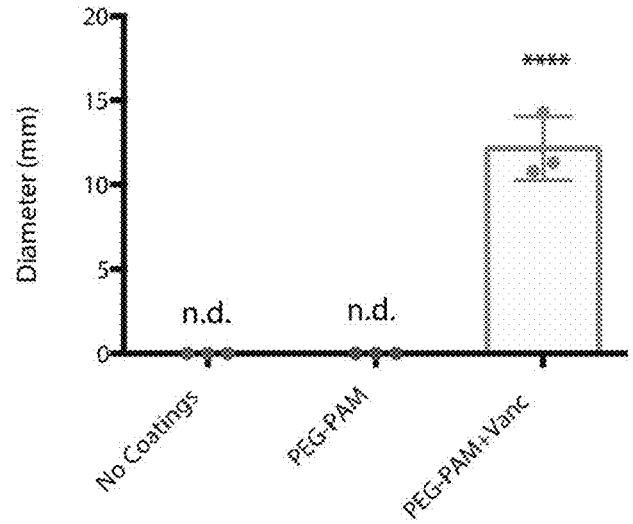
FIG. 17 illustrates the quantification of the diameters of the inhibition zones for the non-coated pin, the pin coated with PEG-PAM only, and the pin coated with PEG-PAM and vancomycin.

Titanium pins that were bare (not coated), coated with PEG-PAM only, and coated with PEG-PMA and vancomycin were tested for their ability to inhibit the growth of *S. aureus*. The respective pins were placed in in a petri dish containing growth media and seeded with *S. aureus*. After 3 days the petri dishes containing the respective coated/non-coated pins were examined for inhibited bacterial growth which could be visualized as a zone or region around the respective pins where bacteria did not grow. The pin containing PEG-PMA and vancomycin showed a clear and marked zone without bacterial growth whereas the other two pins with no coating or PEG-PAM only did not show any sort of similar inhibition zone. FIG. 17 illustrates the quantification of the diameters of the inhibition zones for the non-coated pin, the pin coated with PEG-PAM only, and the pin coated with PEG-PAM and vancomycin.

Figure 18:
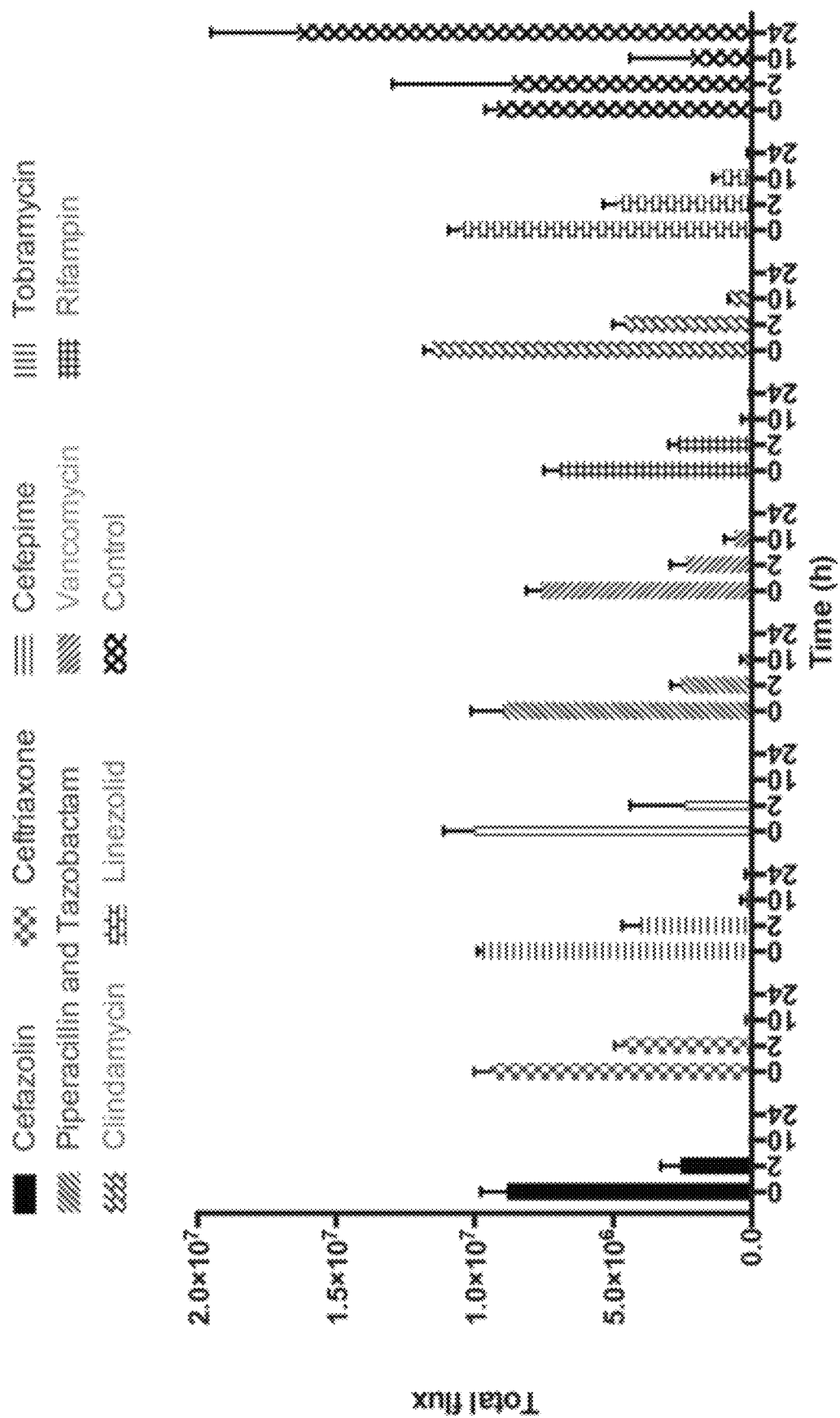
FIG. 18 illustrates the results of the in vitro bioluminescence assay of PEG=PAM coating with the nine (9) different antibiotics tested against S. aureus.

Additional antibiotics were also evaluated using the PEG-PAM system disclosed herein. Here, in vitro bioluminescence assay measurements were performed on titanium pins with PEG-PAM coatings (all single layer) having nine (9) different antibiotics including cefazolin, ceftriaxone, cefepime, tobramycin, piperacillin and tazobactam, vancomycin, rifampin, clindamycin, linezolid, and control. Pins were inserted into the wells of a 96 well plate and then measured using the IVIS® Spectrum in vivo imaging system (PerkinElmer). All of the tested antibiotics loaded into the PEG-PAM system killed *S. aureus* within twenty-four (24) hours. Measurements were taken at 0 hours, two (2) hours, ten (10) hours, and twenty-four 24 hours. FIG. 18 illustrates the results of the in vitro bioluminescence assay of PEG=PAM coating with the nine (9) different antibiotics tested against *S. aureus*.

Figure 19:
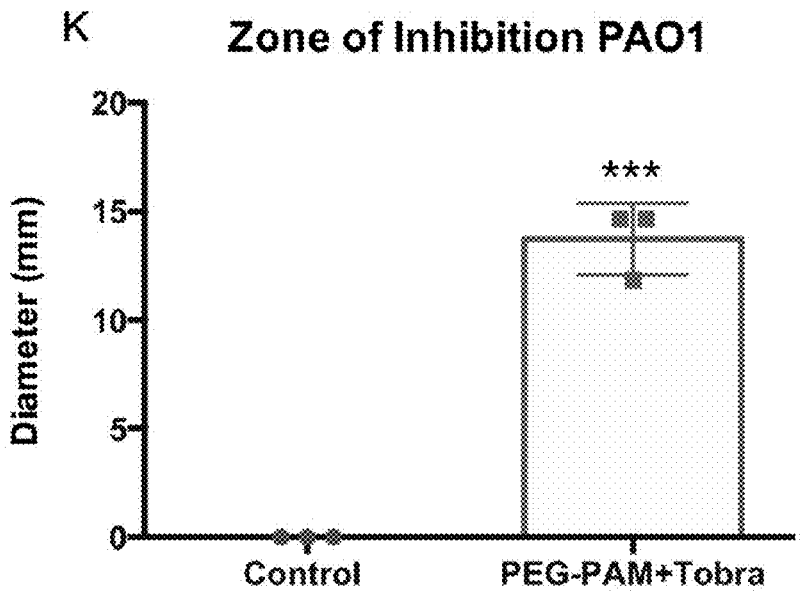
FIG. 19 illustrates the quantification of the diameters of the inhibition zones for a non-coated pin (control) and a pin coated with PEG-PAM loaded with Tobra against Pseudomonas (PAO1 strain).
Figure 20:
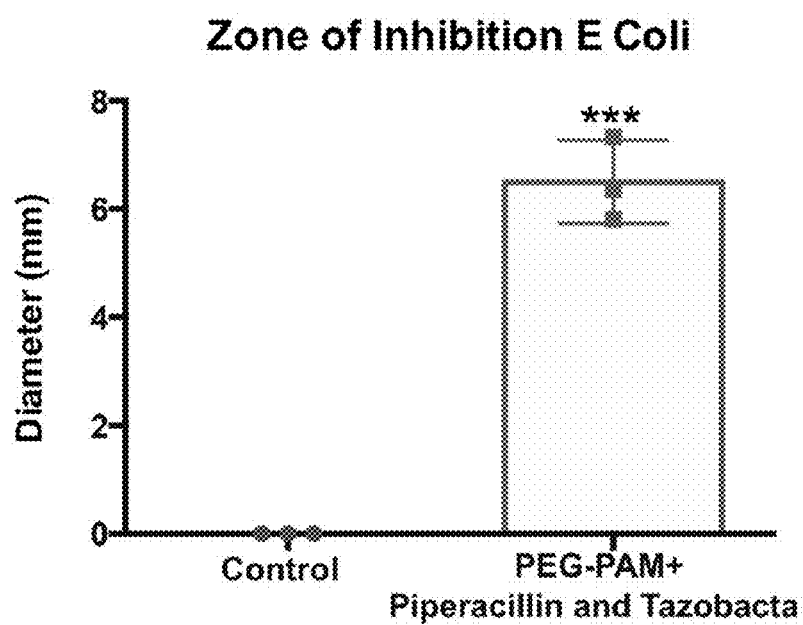
FIG. 20 illustrates the quantification of the diameters of the inhibition zones for a non-coated pin (control) and a pin coated with PEG-PAM, piperacillin and Tazobacta against E. coli.

FIG. 19 illustrates the quantification of the diameters of the inhibition zones for a non-coated pin (control) and a pin coated with PEG-PAM loaded with Tobra against Pseudomonas (PAO1 strain) using similar testing procedure as described above with respect to FIG. 17. FIG. 20 illustrates the quantification of the diameters of the inhibition zones for a non-coated pin (control) and a pin coated with PEG-PAM, piperacillin and Tazobacta against *E. coli* using similar testing procedure as described above with respect to FIG. 17.

Figure 21:
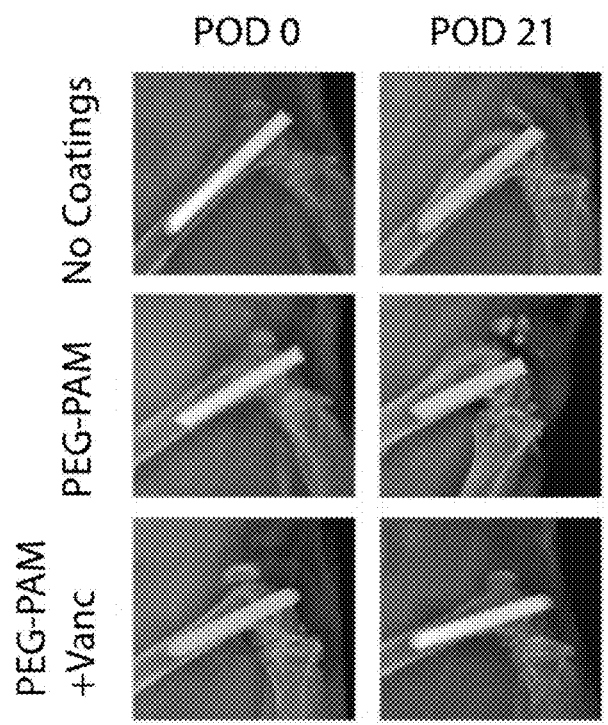
FIG. 21 illustrates lateral radiographs of titanium implants containing no coating, PEG-PAM (no drug), and PEG-PAM loaded with vancomycin. POD stands for post-operative days.

Periprosthetic osteolysis is a serious complication in orthopedic implants, including, for example, total hip replacement (THR) surgery. Osteolysis can lead to prosthesis loosening and periprosthetic fracture. These complications cause significant morbidity and often require additional surgical intervention. To test the ability of the current PEG-PAM platform to reduce the incidence of periprosthetic osteolysis, a titanium pin was implanted into the femur of a mouse. Three different types of pins were implanted: a non-coated implant, an implant coated with PEG-PAM (no drug), and an implant coated with PEG-PAM and vancomycin. As seen in FIG. 21, implants with no coatings or coated with PEG-PAM alone showed a dramatic degree of periprosthetic osteolysis that became evident by post-operative days (POD) 21. In contrast, antibiotic (vancomycin) encapsulated PEG-PAM implants showed no detectable radiographic periprosthetic osteolysis.

Figure 22:
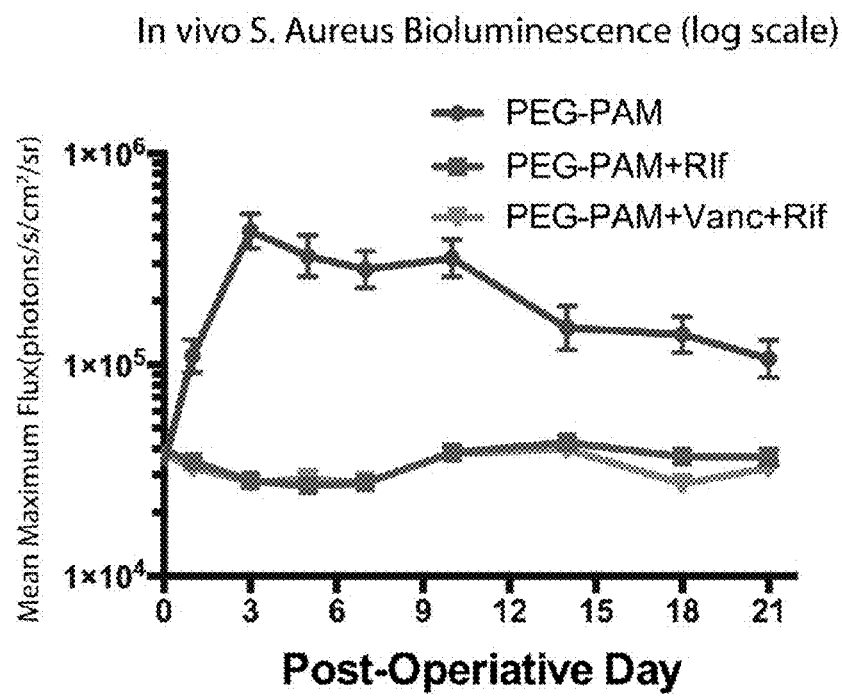
FIG. 22 illustrates the post-operative in vivo bioluminescence analysis of titanium pins implanted into the femur of a mouse. Specifically, a graph of in vivo bioluminescence (mean maximum flus) of S. aureus is shown as a function of time (PODs).

FIG. 22 illustrates the post-operative in vivo bioluminescence analysis of titanium pins implanted into the femur of a mouse. The pins that were implanted had PEG-PAM (no drug), PEG-PAM loaded with rifampin, and PEG-PAM loaded with rifampin and vancomycin. After implantation of the pins, the top, exposed part of the implant was inoculated with *S. aureus* and was analyzed using the IVIS® Spectrum (PerkinElmer) in vivo imaging system. Higher signal levels correspond to high or progressed infection post-surgery. As seen in FIG. 22, both the rifampin and rifampin/vancomycin loaded pins maintain the signal at around baseline which indicates that it clears the injections coming from the bacterial challenge.

Figure 23:
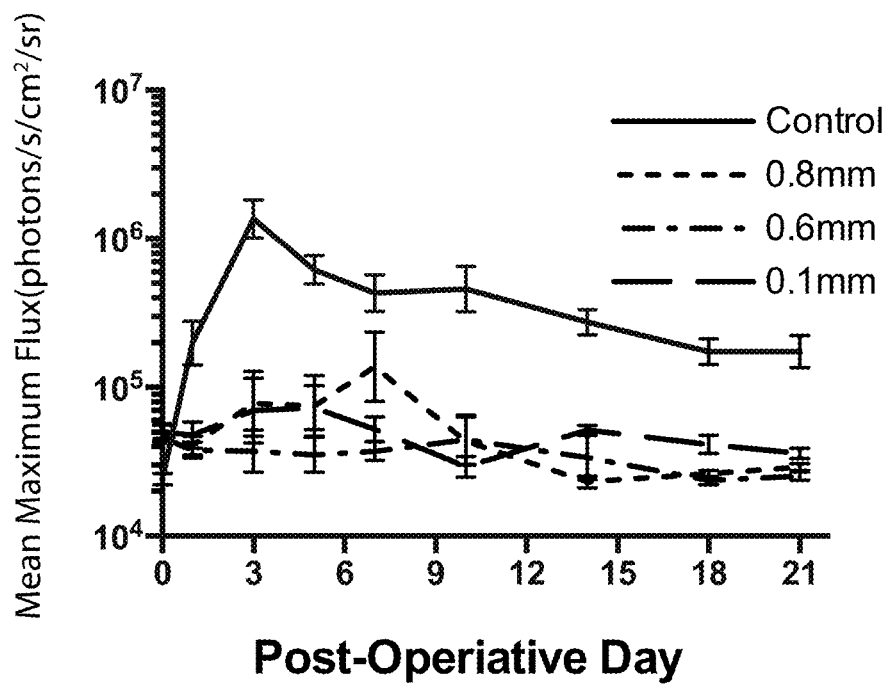
FIG. 23 illustrates the post-operative in vivo bioluminescence analysis of various diameter titanium pins implanted into the femur of a mouse.

FIG. 23 illustrates the post-operative in vivo analysis of various sized stainless steel pins implanted into the femur of a mouse. The pins that where implanted including a control pin (no coating) as well as various diameter pins (0.1 mm, 0.6 mm, 0.8 mm) coated with PEG-PAM loaded vancomycin. After implantation of the pins, the top, exposed part of the implant was inoculated with *S. aureus* and was analyzed using the IVIS® Spectrum as described above. Higher signal levels correspond to high or progressed infection post-surgery. As seen in FIG. 23, the PEG-PAM+vancomycin group of pins (of all sizes) maintains the measured bioluminescence signal at or near baseline levels.

Figure 24:
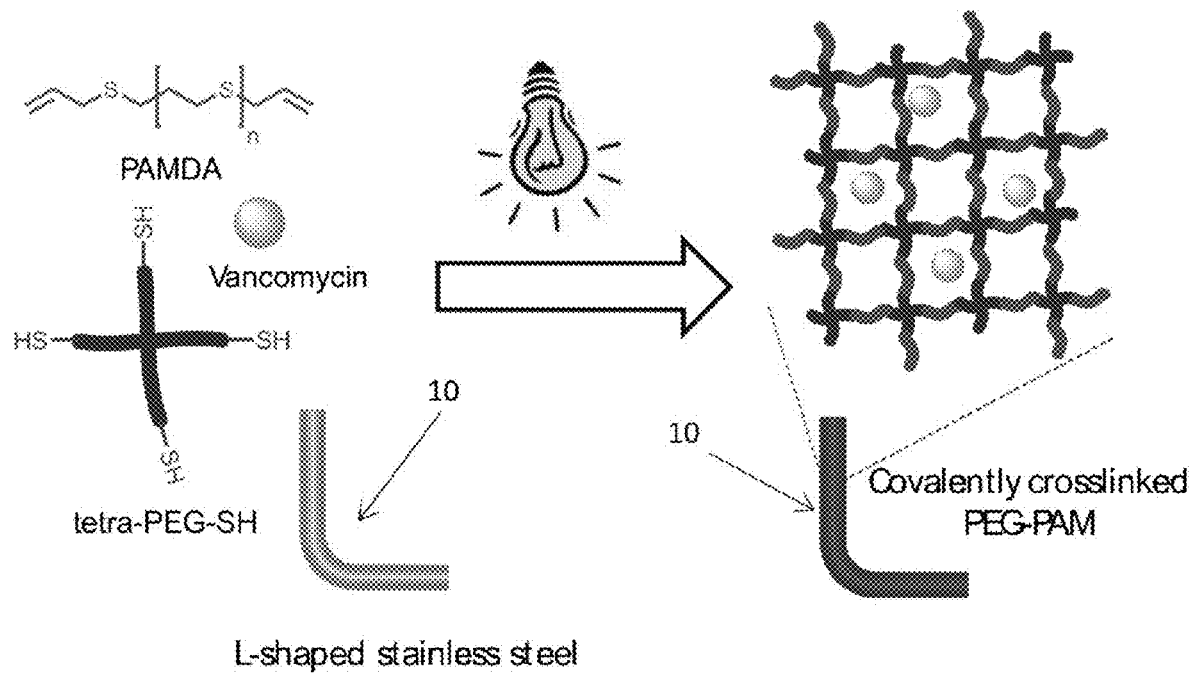
FIG. 24 schematically illustrates the synthesis of a PEG-PAM diallyl (PEG-PAMDA) coating according to one embodiment. The coating is formed on an L-shaped stainless steel medical device or implant for use in spinal applications.

FIG. 24 schematically illustrates the synthesis of PEG-PAM diallyl (PEG-PAMDA) coatings according to one embodiment. As seen in FIG. 24, the PAM that is used to form the PEG-PAMDA includes two allyl terminal ends, i.e., PAM diallyl or PAMDA. In this embodiment, a four arm PEG-thiol molecule was used in conjunction with PAMDA and the drug vancomycin to coat an L-shaped stainless steel pin that was used for spinal surgery. Any number of arms of for the multi-arm PEG may be used. Commercially available PEG with three (3), four (4), five (5), six (6), seven (7), eight (8) or more arms are available and usable with the synthesis method described herein. Crosslinking is initiated using a photoinitiator and source of polymerizing light as explained previously. It was found that standard, single layer PEG-PAM loaded with vancomycin did not work as intended in the in the spinal surgery model. While not wishing to be bound to any particularly theory, it is believed that the single layer PEG-PAM released the vancomycin too quickly into the surrounding tissue. Thus, it was desired to incorporate a stronger, chemically crosslinked coating that would allow the antibiotic to more slowly diffuse out of the coating and into the surrounding environment. PEG-PAMDA allows for slower diffusion of the entrained drug, medicament, or pharmaceutical compound.

Figure 25:
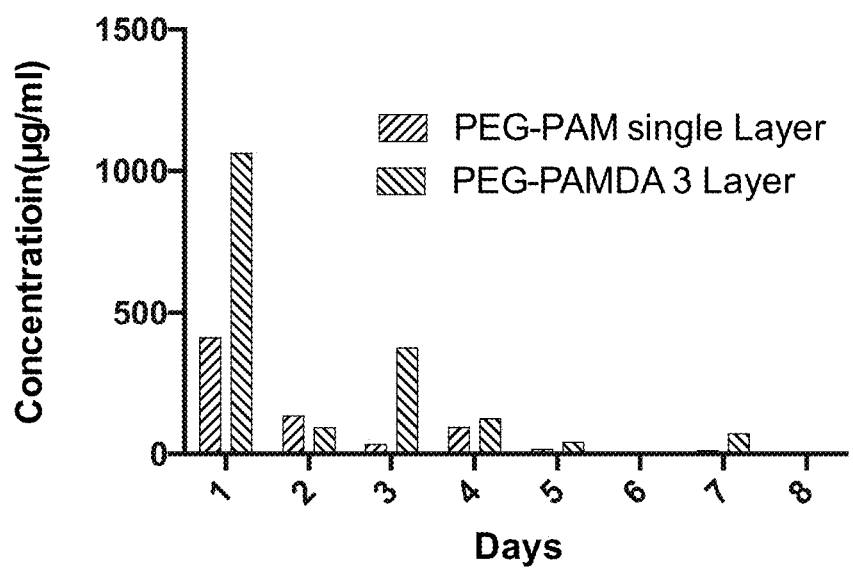
FIG. 25 illustrates the in vitro release of vancomycin from an L-shaped stainless steel pin having a single layer of PEG-PAM. Also illustrated in the in vitro release of vancomycin from an L-shaped stainless steel pin having three layers of PEG-PAMDA.

FIG. 25 illustrates the in vitro release of vancomycin from an L-shaped stainless steel pin having a single layer of PEG-PAM. Also illustrated in the in vitro release of vancomycin from an L-shaped stainless steel pin having three layers of PEG-PAMDA. As seen in FIG. 25, the vancomycin is released much more slowly with the chemically crosslinked PEG-PAMDA coating. Thus, chemical crosslinking of the coating may be employed to control the time release of the drug, medicament, or pharmaceutical compound.

Figure 26:
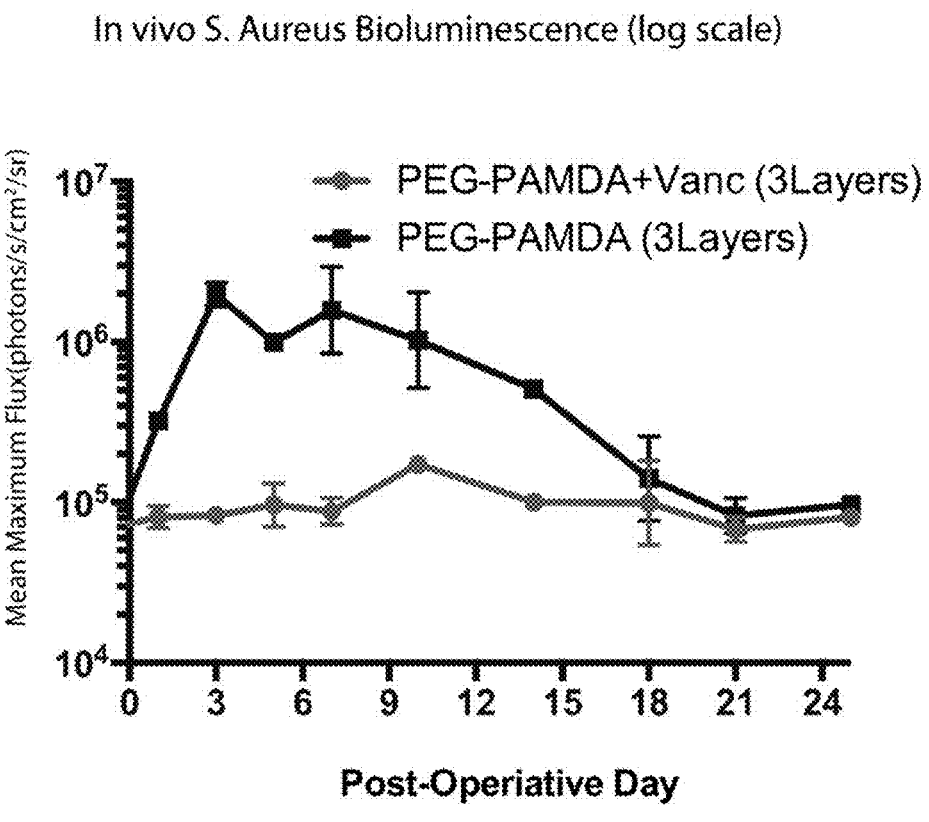
FIG. 26 illustrates the post-operative in vivo analysis of 0.1 mm sized stainless steel L-shaped implants that were implanted in the vertebrae of a mouse. The implants had either PEG-PAMDA (3 layers) and no drug or PEG-PAMDA (3 layers) and vancomycin.

FIG. 26 illustrates the post-operative in vivo analysis of 0.1 mm sized stainless steel L-shaped implants that were implanted in the vertebrae of a mouse. The implants that where implanted and tested for in vivo bioluminescence included an implant coated with three layers of PEG-PAMDA (with no drug) and another implant coated with three layers of PEG-PAMDA and also loaded with vancomycin. After implantation, exposed part of the implant was inoculated with *S. aureus* and was analyzed using the IVIS® Spectrum through 25 days. As seen in FIG. 26, the implant coated with PEG-PAMDA loaded with vancomycin maintained the bioluminescent signal at around baseline levels. Thus, the drug loaded implant was able to clear infections coming from this bacterial challenge.

In the embodiments described above, PEG-PAM hydrogel was assembled by hydrophobic interaction and it was a physical crosslinked hydrogel whose stability was affected by various external stimulus. However, the stability of PEG-PAM hydrogel can be easily tuned through incorporation of chemical crosslinker. Because the terminals of PEG-PAM are allyl group which is a typical substrate for thiol-ene crosslinking, difunctional thiol molecules were employed in the chemical crosslinking reaction to achieve the transformation of physically crosslinked PEG-PAM hydrogel to chemically crosslinked PEG-PAM hydrogel.

Figure 27:
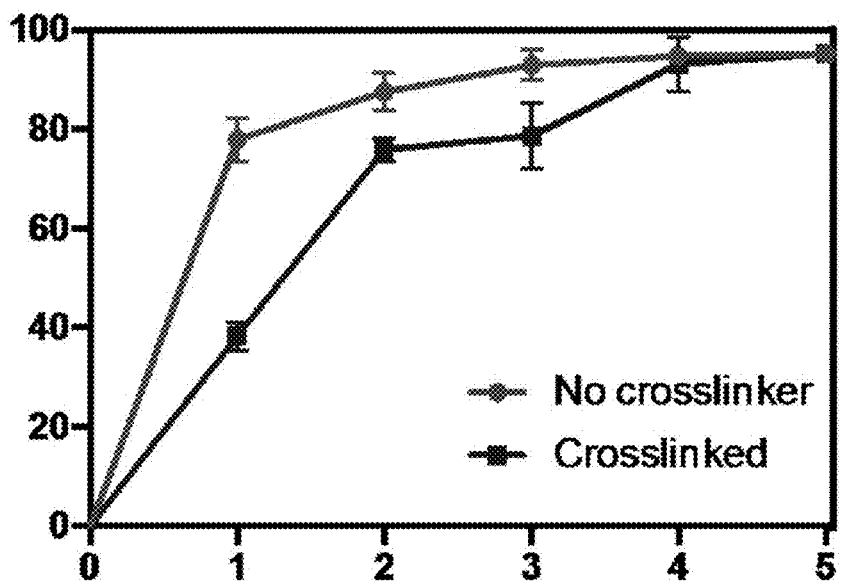
FIG. 27 illustrates a graph of cumulative release of vancomycin as a function of time for PEG-PAM crosslinked with dithiol containing polymers to convert the coating into chemically crosslinked hydrogel.

In a preliminary study, it was confirmed that PEG-PAM could be crosslinked with dithiol containing polymers to convert the coating into chemically crosslinked hydrogel, which would lead to decreased diffusion ability of antibiotics inside of the hydrogel. In this embodiment, PEG-PAM is produced using the first synthesis method described herein, namely, PAM is conjugated with PEG through a thiol reactive groups on the PEG molecule using a catalytic amount of base catalyst such as triethylamine (TEA). The PEG-PAM is then hydrated and PEG-dithiol is added along with the drug (e.g., vancomycin) and photoinitiator (e.g., lithium phenyl-2,4,6-trimethylbenzoylphosphinate (LAP)) were mixed together and 365 nm UV light was used to trigger the crosslinking reaction. In vitro release of vancomycin from PEG-PAM and crosslinked PEG-PAM was monitored by UV-Vis spectrometer. As seen in FIG. 27, after installation of crosslinker (PEG-dithiol), the hydrogel maintained 60% of loaded vancomycin in the gel after day 1, while without the crosslinker, PEG-PAM hydrogel maintains 23% of loaded vancomycin. This confirms the hypothesis that chemical crosslinks will decrease the release rate of antibiotics. Thus, release rate of the drug or pharmaceutical can be controlled through the addition of a crosslinker such as, for example, PEG-dithiol.

Figure 28:
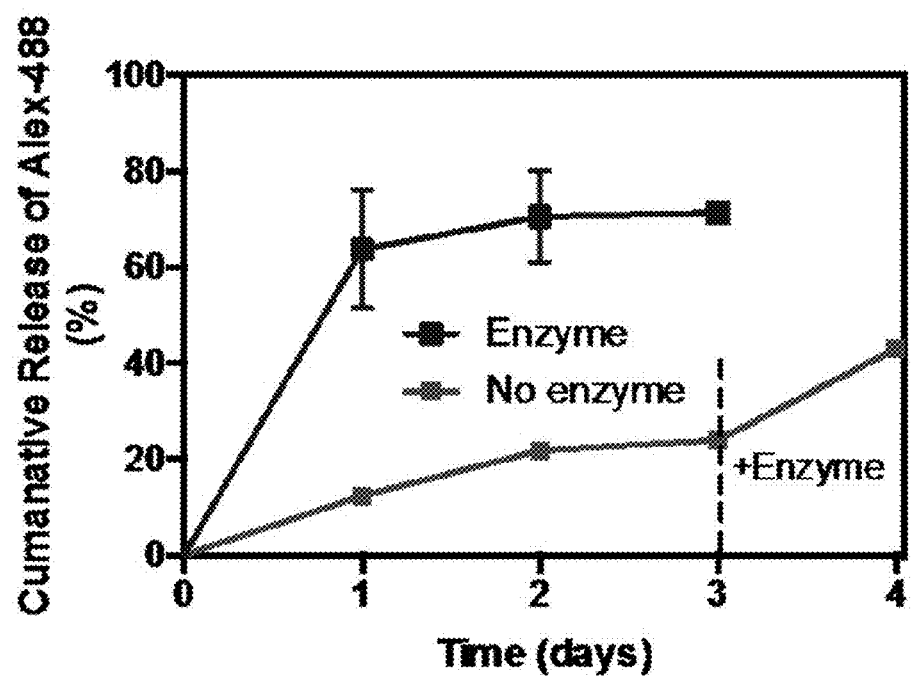
FIG. 28 illustrates a graph of cumulative release of Alex-488 from PEG-PAM hydrogel functionalized with MMP-Alex-488. The presence of collagenase dramatically increases the rate of release.

To demonstrate the versatility of crosslinker, a functional protease degradable peptide was added that would ensure PEG-PAM could be made "smarter", releasing payload in the face of bacterial pressure. Using the same chemistry as that used for crosslinking the PEG-PAM structure, pendent thiol containing species such as peptides containing cysteine were used. This was demonstrated by attaching a fluorescent molecule to the multi-arm PEG-PAM coating through a protease degradable peptide such as a degradable matrix metalloproteinase (MMP). Here, HS-MMP-peptide-Alexa488 was incubated with 4-arm PEG-PAM and exposed to UV light to induce attachment of the peptide to the vinyl groups in PAM. The hydrogel was allowed to form through physical interactions. With reference to FIG. 28, the incubation of the gel in collagenase led to rapid release, achieving ~60% cumulative release in one day. In contrast, less than 10% release was observed in the absence of collagenase at the same one day time period. Thus, the addition of protease degradable peptides to the PEG-PAM coating may be used to accelerate the release of drugs, medicaments, or pharmaceuticals from the PEG-PAM coating.

Note that the eluting properties of the PEG-PAM coating can be adjusted or tuned depending on the desired properties of the coated device or implant. In some embodiments, the drug, medicament, or pharmaceutical may be eluted in a linear fashion over time (this may be a slow release or a rapid release). In other embodiments, an increase or spike in elution may be desired either right after implantation or several days or weeks after implementation. The PEG-PAM elution kinetics may be modified for the appropriate application.

While embodiments of the present invention have been shown and described, various modifications may be made without departing from the scope of the present invention. The invention, therefore, should not be limited except to the following claims and their equivalents.

What is claimed is:

1. A method of coating one or more unmodified metallic surfaces of a medical device comprising:
   providing a mixture of polyallyl mercaptan (PAM), a multi-arm poly(ethylene glycol) (PEG), and a photoinitiator in an organic solvent containing an antibiotic;
   applying the mixture to one or more unmodified metallic surfaces of the medical device;
   waiting a period of time to allow the organic solvent to evaporate; and
   irradiating the mixture with light to form a PEG-PAM coating on the one or more unmodified metallic surfaces of the medical device containing the antibiotic, wherein the PEG-PAM coating is not covalently attached to the one or more unmodified metallic surfaces.

2. The method of claim 1, wherein the multi-arm poly(ethylene glycol) (PEG) has between 3 and 8 arms.

3. The method of claim 1, wherein the multi-arm poly(ethylene glycol) (PEG) comprises a four arm poly(ethylene glycol) (PEG)-thiol and the PEG-PAM coating comprises:

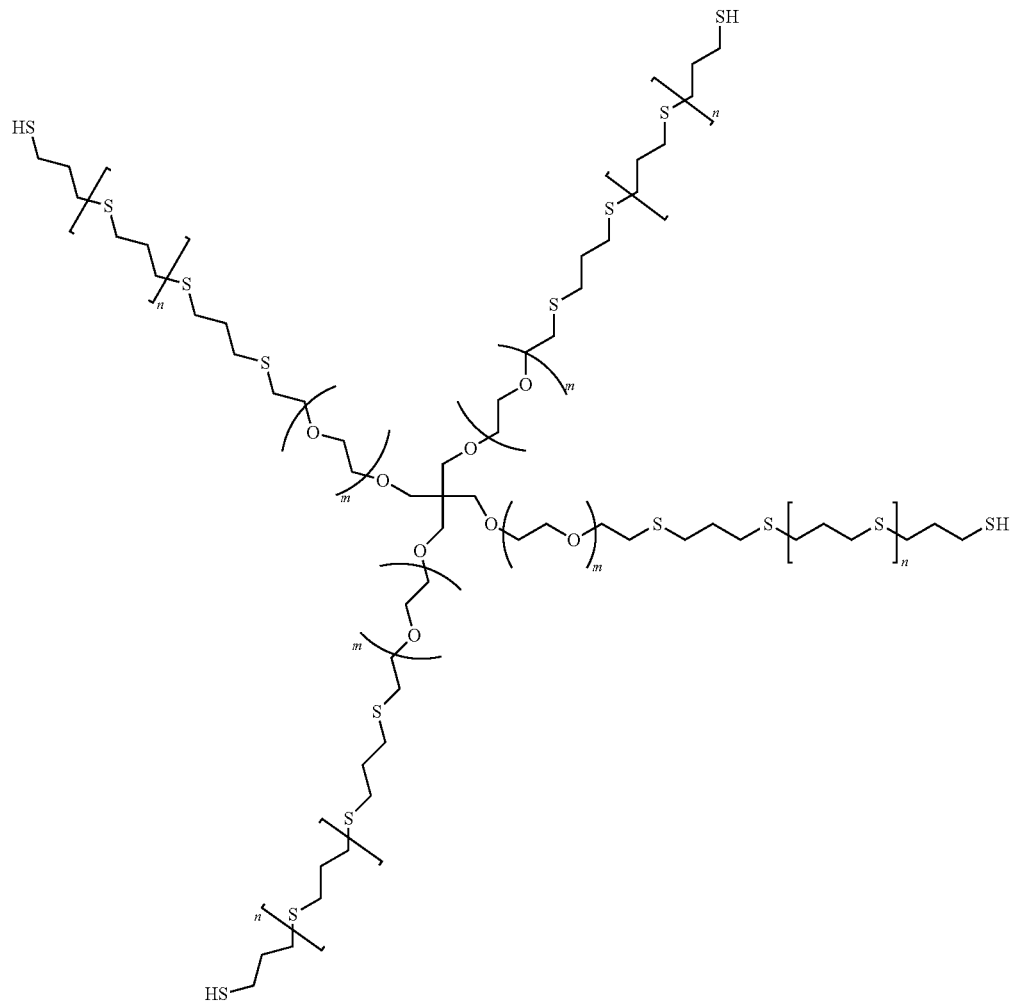

wherein m is between 50 and 500 and n is between 5 and 30.

4. The method of claim 1, wherein the mixture is applied to one or more unmodified metallic surfaces of the medical device by spraying, painting, or dipping.

5. The method of claim 1, wherein the medical device comprises an orthopedic implant, spinal implant, or joint replacement device.

6. The method of claim 1, wherein the PEG-PAM coating is degradable.

7. The method of claim 1, wherein the polyallyl mercaptan (PAM) is thiol-terminated.

8. The method of claim 1, wherein the polyallyl mercaptan (PAM) is allyl-terminated.

9. The method of claim 1, wherein the polyallyl mercaptan (PAM) is both thiol-terminated and allyl-terminated.

* * * * *